United States Patent
Gross et al.

(10) Patent No.: US 6,275,717 B1
(45) Date of Patent: Aug. 14, 2001

(54) DEVICE AND METHOD OF CALIBRATING AND TESTING A SENSOR FOR IN VIVO MEASUREMENT OF AN ANALYTE

(75) Inventors: Joseph Gross, Moshav Mazor; Meir Reingewirtz, Ramat Hasharon; Moshe George Katz, Rishon Lezion, all of (IL)

(73) Assignee: Elan Corporation, plc, Dublin (IR)

( * ) Notice: Subject to any disclaimer, the term of this patent is extended or adjusted under 35 U.S.C. 154(b) by 0 days.

(21) Appl. No.: 09/102,840

(22) Filed: Jun. 23, 1998

(30) Foreign Application Priority Data

Jun. 16, 1997 (IE) .......................................... 970443

(51) Int. Cl.[7] ................. A61B 5/00; A61B 5/05

(52) U.S. Cl. ................. 600/345; 600/347; 600/309

(58) Field of Search ..................... 600/309, 345–346, 600/347–348, 354, 355, 353, 358, 362, 365–366

(56) References Cited

U.S. PATENT DOCUMENTS

| | | |
|---|---|---|
| 2,408,323 | 9/1946 | Lockhart et al. . |
| 2,576,951 | 12/1951 | Lockhart et al. . |
| 3,964,482 | 6/1976 | Gerstel et al. . |
| 4,340,458 | 7/1982 | Lerner et al. . |
| 4,396,464 | 8/1983 | Giner et al. . |
| 4,515,584 | 5/1985 | Abe et al. . |
| 4,627,445 | 12/1986 | Garcia et al. . |
| 4,637,403 | 1/1987 | Garcia et al. . |
| 4,684,365 | 8/1987 | Reinicke . |
| 4,684,367 | 8/1987 | Schaffer et al. . |
| 4,697,622 | 10/1987 | Swift et al. . |
| 4,805,624 | 2/1989 | Yao et al. . |
| 4,886,499 | 12/1989 | Cirelli et al. . |
| 4,902,278 | 2/1990 | Maget et al. . |
| 4,953,552 | 9/1990 | DeMarzo . |
| 4,970,145 | 11/1990 | Bennetto et al. . |
| 5,070,886 | 12/1991 | Mitchen et al. . |
| 5,079,421 | 1/1992 | Knudson et al. . |
| 5,090,963 | 2/1992 | Gross et al. . |
| 5,122,456 | 6/1992 | Bennetto et al. . |
| 5,160,418 | 11/1992 | Mullen . |
| 5,165,407 | 11/1992 | Wilson et al. . |
| 5,193,545 | 3/1993 | Marsoner et al. . |
| 5,231,028 | 7/1993 | Mullen . |
| 5,242,406 | 9/1993 | Gross et al. . |
| 5,267,152 | * 11/1993 | Yang et al. ..................... 364/413.09 |
| 5,286,362 | 2/1994 | Hoenes et al. . |
| 5,298,022 | 3/1994 | Bernardi . |
| 5,322,063 | 6/1994 | Allen et al. . |
| 5,387,328 | 2/1995 | Sohn . |
| 5,399,245 | 3/1995 | Fedkiw, Jr. . |

(List continued on next page.)

FOREIGN PATENT DOCUMENTS

| | | |
|---|---|---|
| 4221848 | 1/1994 | (DE) . |
| 0 098 592 | 1/1984 | (EP) . |
| 0 209 677 | 1/1987 | (EP) . |
| 0 396 788 | 11/1990 | (EP) ............................. C12M/1/40 |
| 0 401 179 | 12/1990 | (EP) . |
| WO 94/13203 | 6/1994 | (WO) . |
| WO 95/10223 | 4/1995 | (WO) . |
| WO 95/13838 | 5/1995 | (WO) . |
| WO 96/06019 | 2/1996 | (WO) . |
| WO 95/25089 | 8/1996 | (WO) . |
| WO 96/25088 | 8/1996 | (WO) . |

*Primary Examiner*—Cary O'Connor
*Assistant Examiner*—Navin Natnithithadha
(74) *Attorney, Agent, or Firm*—Kathleen L. Maher

(57) ABSTRACT

A method of calibrating an analyte sensor in vivo, by providing a first predetermined stimulus to the sensor when the sensor is applied to a subject to produce a first sensor signal, measuring the first sensor signal, and determining a calibration function based on the first measured sensor signal resulting from the predetermined stimulus. The calibration function, when applied to further signals received from the sensor, can be used to provide a calibrated output.

59 Claims, 12 Drawing Sheets

U.S. PATENT DOCUMENTS

| | | |
|---|---|---|
| 5,422,246 | 6/1995 | Koopal et al. . |
| 5,425,361 | 6/1995 | Fenzlein et al. . |
| 5,443,701 | 8/1995 | Willner et al. . |
| 5,497,772 | 3/1996 | Schulman et al. . |
| 5,515,848 | 5/1996 | Corbett, III et al. . |
| 5,527,288 | 6/1996 | Gross et al. . |
| 5,543,024 | 8/1996 | Hanazato et al. . |
| 5,545,143 | 8/1996 | Fischell . |
| 5,547,467 | 8/1996 | Pliquett . |
| 5,562,613 | 10/1996 | Kaldany . |
| 5,567,290 | 10/1996 | Vadgama et al. . |
| 5,569,186 | 10/1996 | Lord et al. . |
| 5,697,366 * | 12/1997 | Kimball et al. ............... 600/309 |
| 5,976,085 * | 11/1999 | Kimball et al. ............... 600/309 |

* cited by examiner

DEVICE AND METHOD OF CALIBRATING AND TESTING A SENSOR FOR IN VIVO MEASUREMENT OF AN ANALYTE

TECHNICAL FIELD

This invention relates to devices and methods for measuring an analyte in vivo, and in particular to sensors for use in such devices and methods.

BACKGROUND OF THE INVENTION

Our WO 96/14026, incorporated herein by reference, describes an analyte-controlled liquid delivery device and analyte monitor in which an analyte such as glucose is detected by a platinum-iridium sensor needle having an enzymatic coating such as glucose oxidase. The sensor needle is typically located on a housing having a lower surface for application to the skin of a subject. Glucose in the presence of the enzymatic coating undergoes a reaction with oxygen, and one of the by-products of the reaction is hydrogen peroxide. This in turn is broken down by the platinum in the sensor needle which forms an electrode of an electrical circuit. The level of concentration of glucose is proportional to the magnitude of the current. Thus, the magnitude of the current through the electrical circuit can be used to determine the concentration of glucose.

It has been found that when enzymatic sensors are mass-produced (like many other products), there are slight variations between batches, although individual sensors in each batch are identical. Accordingly to avoid errors in measurements made using such sensors, each production batch can be calibrated.

One method of calibrating such sensors is to use them to measure a standard solution of the analyte for which they are intended, and thereby determining the signal strength achieved from a known concentration of analyte. By making one or more measurements in this way for a statistically valid sample of sensors in a batch it is possible to determine a calibration function which can in theory be used to derive the analyte concentration in vivo from the measured signal.

However, due to the sensitive nature of enzymes, the performance of a sensor may vary over the shelf life of the sensor. Additionally, when the sensor is actually used, it is in a different environment from that in which the batch was calibrated. The sensor will form part of a system in use which is partly biological and which will vary between individual subjects. For example, the laboratory batch calibration function may not take account of the presence of unwanted substances in vivo which give a false background signal.

For these reasons, it has been found that sensors characterised by a laboratory batch calibration are unsatisfactory because such calibration does not permit the performance of the sensor in vivo to be accurately predicted in all cases.

It is thus an object of the present invention to provide a quick and accurate method of in vivo calibration of an analyte sensor.

A further problem associated with enzymatic sensors is that they are subject to a deterioration in performance. This can happen as a result of the enzymatic material being physically or chemically degraded, or as a result of a build up of biological material on the sensor, for example. In WO 96/14026, incorporated herein by reference, a method of detecting a decrease in the performance level of a sensor is disclosed. In this method, a pulsatile sampling technique is used in which pulses of current are detected at or about a peak value and at or about a base line value. The ratio of the two measured currents was found to be independent of the concentration of the analyte being measured, such that if this ratio was found to change over time, one could deduce that the performance of the sensor had changed in some way (usually due to degradation). The present invention seeks to provide an alternative and more reliable method of monitoring sensor performance and degradation.

The present invention seeks to provide an alternative method of testing a sensor to detect changes in the sensor performance.

In measuring an analyte by means of a chemical or electrochemical reaction which requires oxygen, difficulties can arise when the measurement must be carried out in vivo. The quantity of dissolved oxygen in the blood or tissue at the location of the sensor may not be sufficient. If there is an insufficient supply of oxygen, then the rate of reaction of the analyte (and hence the detected level of analyte) may be limited by the available oxygen. This can give rise to false readings which are potentially extremely dangerous, such as in cases where the measured analyte level is used as the basis for the possible administration of a therapeutic agent.

In the case of glucose, this could lead to a diabetic patient being measured as having normal glucose levels when in fact glucose levels had increased to a point where insulin is required to reduce those levels. An error in detection of the glucose level can therefore give rise to problems and indeed dangers to diabetic patients. The same is also true in respect of other substances for which there is a medical need for in vivo analysis and measurement. For these reasons, it is clearly advantageous and important to improve the performance and accuracy of such devices and sensors.

SUMMARY OF THE INVENTION

Accordingly, the present invention provides for a method of calibrating an analyte sensor in vivo, comprising the steps of:

(a) providing a first predetermined stimulus to the sensor when the sensor is applied to a subject to produce a first sensor signal;

(b) measuring the first sensor signal; and (c) determining a calibration function based on the first measured sensor signal resulting from the predetermined stimulus, whereby the calibration function when applied to further signals received from the sensor can be used to provide a calibrated output.

The provision of a predetermined stimulus in vivo enables the sensor response to be calibrated, since the theoretical response of the sensor to such a stimulus can be determined beforehand. Accordingly, the method according to the invention provides a way of using the response attained from a predetermined stimulus to evaluate the response to subsequent stimuli, i.e. actual measurements recorded by the sensor in vivo, taking into account the condition of the sensor and the conditions encountered in use.

Preferably, the first predetermined stimulus is generated by providing a supply of material to which the sensor is sensitive, such that the material stimulates the sensor when the sensor is applied to a subject.

By supplying a material to which the sensor is sensitive, one can reliably generate a stimulus for the sensor which can be accurately predetermined beforehand.

Suitably, the material is provided in the vicinity of the sensor in a form in which it is soluble in biological fluids present in the area of the subject to which the sensor is applied.

A soluble material will be released to the sensor upon application to the body, and since the speed of dissolution and the transport of dissolved material in the body can be accurately predicted, so can the time at which the material reaches the sensor and the concentration of material thereby encountered by the sensor.

In preferred embodiments, the material comprises an analyte or a precursor or derivative thereof.

The important factor is that the sensor generates a reliable response to whichever material is chosen, but by choosing the analyte or a closely related substance as the relevant material, a relatively simple sensor which is only required to be sensitive to one substance or a small range of substances can be used. As a further example, instead of using the analyte to be detected, one could choose a salt of the analyte which exhibits a high solubility in vivo.

Suitably, the predetermined stimulus is adapted to saturate the sensor such that the first signal is a maximum signal.

When a sensor is such that it can be saturated by a sufficiently large stimulus, it can be preferable to use this phenomenon in calibrating the sensor as it enables a reproducible first predetermined stimulus, i.e. a saturation stimulus to be provided in all cases, thereby removing uncertainty as to whether the means for providing a predetermined stimulus will in fact achieve exactly the right level of uncertainty.

In preferred embodiments, the method according to the invention further comprises the steps of providing a second predetermined stimulus to the sensor so as to produce a second sensor signal and measuring the second sensor signal, such that the determination of the calibration function is based on the first and second measured sensor signals.

It has been found that a more accurate calibration is achieved when two signals are received from predetermined stimuli, as this generally allows the sensor to be calibrated over a working range with accuracy.

Preferably, the second sensor signal is a base line signal measured when substantially no analyte is in the vicinity of the sensor.

The use of a base line signal in combination with a saturation signal is preferred as this enables the sensor to be calibrated for all useful signals, and these two endpoints can enable the sensor reaction to be extrapolated for intermediate points.

Suitably, the second predetermined stimulus is provided by consuming substantially all of the analyte in the vicinity of the sensor.

The consumption of analyte in the vicinity of the needle causes the sensor to generate a base line signal which is attributable only to factors other than the presence of analyte (e.g. extraneous substances which generate false analyte measurements, residual background signals generated by the sensor, etc.).

Preferably, the analyte is measured by the sensor by means of an electrochemical reaction, with the sensor forming part of an electrical circuit, and the analyte is consumed by providing a current through the circuit which causes the analyte to undergo the electrochemical reaction, with the measurement of the second sensor signal being carried out shortly after the analyte is consumed.

The advantage of this method of consuming analyte is that the apparatus required to consume the analyte can be the same apparatus which is present in any event as part of the sensor and associated components.

Preferably, the first and second signals constitute known points on a measured performance curve describing the measured performance of the sensor, and the calibration function correlates the measured performance curve with a theoretical sensor performance curve for which there is stored a calibrated output, such that any further sensor signal measurement from the sensor can be calibrated by correlating the point on the measured performance curve to which the measurement relates with a corresponding point on the theoretical sensor performance curve, and hence with the corresponding calibrated output.

The theoretical sensor performance curve can be determined during the design of the sensor, can be measured for individual sensors during production, or can be measured for a manufactured batch of sensors on a statistical basis. Two curves having basic common parameters (such as a common shape) can thus be correlated to one another by comparing known points on each curve and extrapolating for subsequently measured points.

Preferably, the known points on a curve describing the measured performance of the sensor are endpoints of the curve. If the curve has a well defined shape, two endpoints may enable the intervening points to be calculated with accuracy. Indeed if one of the endpoints is always exactly zero (as in the case of a linear curve whose only variable is the slope), then a single saturation endpoint may describe the entire curve mathematically.

As will be further described below, a particularly preferred analyte is glucose. The advantages of having a reliable alternative method of measuring glucose in vivo are plain given the number of diabetics for whom blood sampling tests several times daily are a fact of life. The most common method of blood sampling currently in use is a procedure in which the skin must be punctured on every occasion. Until now, the use of a continuous monitoring system was hampered by calibration difficulties, and so the present invention provides a way of removing this difficulty.

The invention thus provides also a method of measuring an analyte in vivo comprising the steps of applying a sensor to a subject, calibrating the sensor according to the invention, and providing a calibrated output of any further measurements made by the sensor based on the calibration function.

In another aspect, the invention provides a device for the in vivo measurement of an analyte, comprising:
   (a) an in vivo sensor for measuring the analyte and providing a signal in response to the measurement of the analyte;
   (b) means for providing a first predetermined stimulus to the sensor when the sensor is applied to a subject so as to produce a first sensor signal; and
   (c) electronic circuitry associated with the sensor for receiving the signal and providing a calibrated output based on the signal, wherein the electronic circuitry includes means for determining a calibration function for the sensor based on the first measured sensor signal resulting from the predetermined stimulus;
such that the function when applied to further signals received from the sensor can be used to provide a calibrated output.

As the skilled person will appreciate, this device is adapted to carry out the calibration method discussed above, and therefore has many of the same advantages associated therewith. Further features of such a device are set out below, the advantages of which will in many cases also be apparent from the above discussion.

Preferably, the means for providing a first predetermined stimulus to the sensor comprises a supply of material associated with the sensor such when the sensor is applied to a subject, the sensor is sensitive to the material.

Further, preferably, the supply of material is associated with a permeable protective coating provided on the sensor.

In a preferred embodiment, the supply of material is provided in an amount sufficient to saturate the sensor and thereby generate a maximum signal which can be used to calibrate the sensor.

Preferably, the sensor comprises an element which is adapted to be inserted subcutaneously, intradermally, intravenously or by surgical implantation into the subject, and the supply of material is provided on the sensor in soluble form.

Thus, the sensor can be provided in the form of a needle on a device which can be affixed to the skin painlessly and worn unobtrusively, such that the sensor penetrates the skin to a predetermined depth. By choosing the site at which the device is to be affixed, a good degree of uniformity between individuals is ensured.

Presently preferred devices of this type comprise a housing having a lower surface for application to the skin of a subject, the sensor being in the form of a needle extending from the housing such that the sensor penetrates the skin of the subject when the device is applied thereto.

Suitably, means are provided for generating a base line signal corresponding to the signal obtained when substantially no analyte is present in the vicinity of the needle, and the base line signal is used to calibrate the sensor.

Preferably, the means for generating a base line signal comprises a voltage generator which forms part of the electronic circuitry, and the base line signal is provided by passing a current in the vicinity of the needle which eliminates the analyte or a chemical substance used in the measurement of the analyte.

Further, preferably, the analyte to be detected by the device is glucose.

The invention also provides a method for the in vivo testing of an analyte sensor which is provided to a subject as an electrode of an electrical circuit, comprising the steps of:
  (a) applying a potential to the electrode and varying the electrode potential so as to cause the electrode current to undergo at least part of a cycle which exhibits hysteresis;
  (b) measuring and recording a plurality of current values on the hysteresis cycle;
  (c) calculating a characteristic point on the hysteresis curve from the plurality of current values; and
  (e) comparing the characteristic point with a stored value and determining from this comparison whether the sensor meets a predetermined condition.

It has been found that degradation of an electrode in use is in many cases accompanied by changes in the current-voltage response of the electrical circuit of which the electrode forms part. At any given voltage (e.g. the voltage used in the measurement of the analyte), such changes could be interpreted as a change in analyte levels. Surprisingly, however, the shape of a hysteresis cycle for the electrode will change, and if a characteristic point on such a cycle has been identified when the sensor is operating correctly, deterioration of the sensor may be identified by a change in the current-voltage response at such a characteristic point.

Suitably, the characteristic point is a nodal point on the hysteresis curve, with the nodal point preferably defined as a voltage for which the current value is independent of the analyte concentration in the vicinity of the sensor when the sensor is operating correctly.

Suitably, steps (a)–(e) of the method of testing the sensor needle are repeated periodically. This allows the sensor to be repeatedly tested while in use, thereby monitoring the sensor for deviations from the expected performance.

Preferably, an initial iteration of steps (a)–(d) yields a value for the characteristic point which is stored for comparative subsequent use.

Thus, rather than using a laboratory calibration to determine the characteristic point(s), this can be done in vivo for a more accurate determination.

Further, preferably, the initial iteration is repeated a plurality of times shortly after the sensor has been applied to the subject, and a supply of the analyte to be measured is provided to the sensor in varying concentrations during the repetition of the iterations.

Most preferably, the analyte is supplied on the sensor in such a manner that it is released upon application of the sensor to the subject, and wherein the varying concentrations of analyte are achieved by consuming the analyte in a reaction or allowing the analyte to diffuse within the body of the subject.

In this manner, the determination of a characteristic point can be carried out at the time that the sensor is being calibrated in vivo, since as described above the in vivo calibration may employ varying levels in analyte concentration at the sensor, and these varying analyte levels also enable the current-voltage response to be measured at different analyte levels as part of repeated hysteresis cycles.

The method suitably comprises the further step of providing an indicator if it is determined that the sensor does not meet the predetermined condition. Preferably, the indicator comprises an audible alarm.

In another aspect, the invention provides a device for the in vivo measurement of an analyte, comprising:
  (a) an in vivo sensor for measuring the analyte and providing a signal in response to the measurement of the analyte;
  (b) electronic circuitry associated with the sensor for receiving the signal and providing a calibrated output based on the signal;
  (c) an electrical circuit in which the sensor acts as an electrode, the electrical circuit comprising means for energising the electrode to a predetermined potential and for measuring and recording the resultant current through the electrode;
  (d) means for varying the electrode potential so as to cause the current to undergo at least part of a hysteresis cycle;
  (e) means for calculating a characteristic point on the hysteresis curve from the recorded current measurements; and
  (f) means for comparing the characteristic point with a stored value and for determining from this comparison whether the sensor meets a predetermined condition.

Such a device is adapted for use in the testing method according to the invention and the advantages of this testing method as set out above also apply in large part to the corresponding device, as well as to many of the preferred features set out below.

Thus, preferably, the characteristic point is a nodal point on the hysteresis curve, and the nodal point is preferably defined as a voltage for which the current value on the hysteresis curve is independent of the analyte concentration in the vicinity of the sensor when the sensor is functioning correctly.

The device preferably comprises a memory for storing the value of a characteristic point determined on an initial iteration of measurements of current values.

A further preferred feature is means for providing an alarm if it is determined that the sensor does not meet the predetermined condition.

The invention provides, in another aspect, a method for the in vivo measurement of an analyte, comprising:

(a) providing an in vivo sensor, which acts as an electrode of an electrical circuit, to a subject for measuring the analyte, wherein the operation of the sensor is dependent on a reaction in which oxygen is required;

(b) passing a voltage through the electrode, the voltage being of a magnitude and duration sufficient to cause the electrolysis of a chemical species present in the vicinity of the sensor so as to generate oxygen;

(c) measuring the signal produced by the sensor in response to the oxygen-dependent reaction; and (d) repeating steps (b) and (c) periodically.

The use of electrolysis of a substance to generate oxygen can overcome the problems of a deficiency in oxygen inside the body, and thereby increase the accuracy of the sensor. It effectively raises the maximum level of analyte measurable where a lack of oxygen is the limiting factor in analyte measurement.

Preferably, water is the chemical species present in the vicinity of the sensor which is electrolysed to provide oxygen.

Preferably, step (b) continues for a duration sufficient to generate oxygen in an excess stoichiometric ratio relative to the analyte being measured at the sensor. Thus, if the measurement of analyte is achieved by a pulsatile sampling technique, oxygen generating pulses can be interleaved with the measurement pulses to ensure that at all times a sufficient amount of oxygen is present.

The invention also provides a device for the in vivo measurement of an analyte, comprising:

(a) an in vivo sensor for measuring the analyte and providing a signal in response to the measurement of the analyte, wherein the operation of the sensor is dependent on a reaction in which oxygen is required;

(b) electronic circuitry associated with the sensor for receiving the signal and providing a calibrated output based on the signal;

(c) an electrical circuit in which the sensor acts as an electrode, the electrical circuit comprising means for energising the electrode to a voltage which is of a magnitude and duration sufficient to cause the electrolysis of a chemical species present in the vicinity of the sensor to provide oxygen; and (d) means for alternately generating oxygen by electrolysis and measuring the analyte by allowing the generated oxygen to take part in the reaction.

For any of the devices according to the invention, there may suitably be provided means for delivering a substance to the subject in response to the measured analyte values.

Thus, the device may comprise a pump containing insulin which may be pumped at a controllable rate in response to measured glucose levels. The principles of operation of such a pump will be known to the person skilled in the art, and suitable examples are disclosed in WO 96/14026, incorporated herein by reference.

Preferably the substance is a medicament suitable to correct a condition in the patient for which the analyte is an indicating agent.

The invention further provides a device for calibrating an analyte sensor in vivo, comprising:

(a) a sensor for application to a subject;

(b) means for providing a first predetermined stimulus to the sensor to produce a first sensor signal;

(c) means for measuring the first sensor signal; and (d) means for determining a calibration function based on the first measured sensor signal resulting from the predetermined stimulus, whereby the calibration function when applied to further signals received from the sensor can be used to provide a calibrated output.

Preferably, the means for providing the first predetermined stimulus comprises a supply of material to which the sensor is sensitive, such that the material stimulates the sensor when the sensor is applied to a subject.

Further, preferably, the material is soluble in biological fluids present in the area of the subject to which the sensor is applied.

Suitably, the material comprises an analyte or a precursor or derivative thereof.

Preferably, the predetermined stimulus is adapted to saturate the sensor such that the first signal is a maximum signal.

In preferred embodiments, the device further comprises means for providing a second predetermined stimulus to the sensor so as to produce a second sensor signal and means for measuring the second sensor signal, such that the means for determination of the calibration function determines a calibration function based on the first and second measured sensor signals.

Preferably, the second sensor signal is a base line signal measured when substantially no analyte is in the vicinity of the sensor.

Suitably, the second predetermined stimulus is provided by consuming substantially all of the analyte in the vicinity of the sensor.

Preferably, the first and second signals constitute known points on a measured performance curve describing the measured performance of the sensor, and the calibration function correlates the measured performance curve with a theoretical sensor performance curve for which there is stored a calibrated output, such that any further sensor signal measurement from the sensor can be calibrated by correlating the point on the measured performance curve to which the measurement relates with a corresponding point on the theoretical sensor performance curve, and hence with the corresponding calibrated output.

Preferably, the known points on a curve describing the measured performance of the sensor are endpoints of the curve.

The invention also provides a device for measuring an analyte in vivo comprising means for applying a sensor to a subject, means for calibrating the sensor according to the method of the present invention, and means for providing a calibrated output of any further measurements made by the sensor based on the calibration function.

Other objects, features and advantages of the present invention will become apparent upon reading the following detailed description of the embodiments of the invention, when taken in conjunction with the drawings and appended claims.

BRIEF DESCRIPTION OF THE DRAWINGS

The invention will be further illustrated by the following description of embodiments thereof, given by way of example only with reference to the accompanying drawings, in which.

DETAILED DESCRIPTION OF THE INVENTION

1. Construction

Figure 1A:
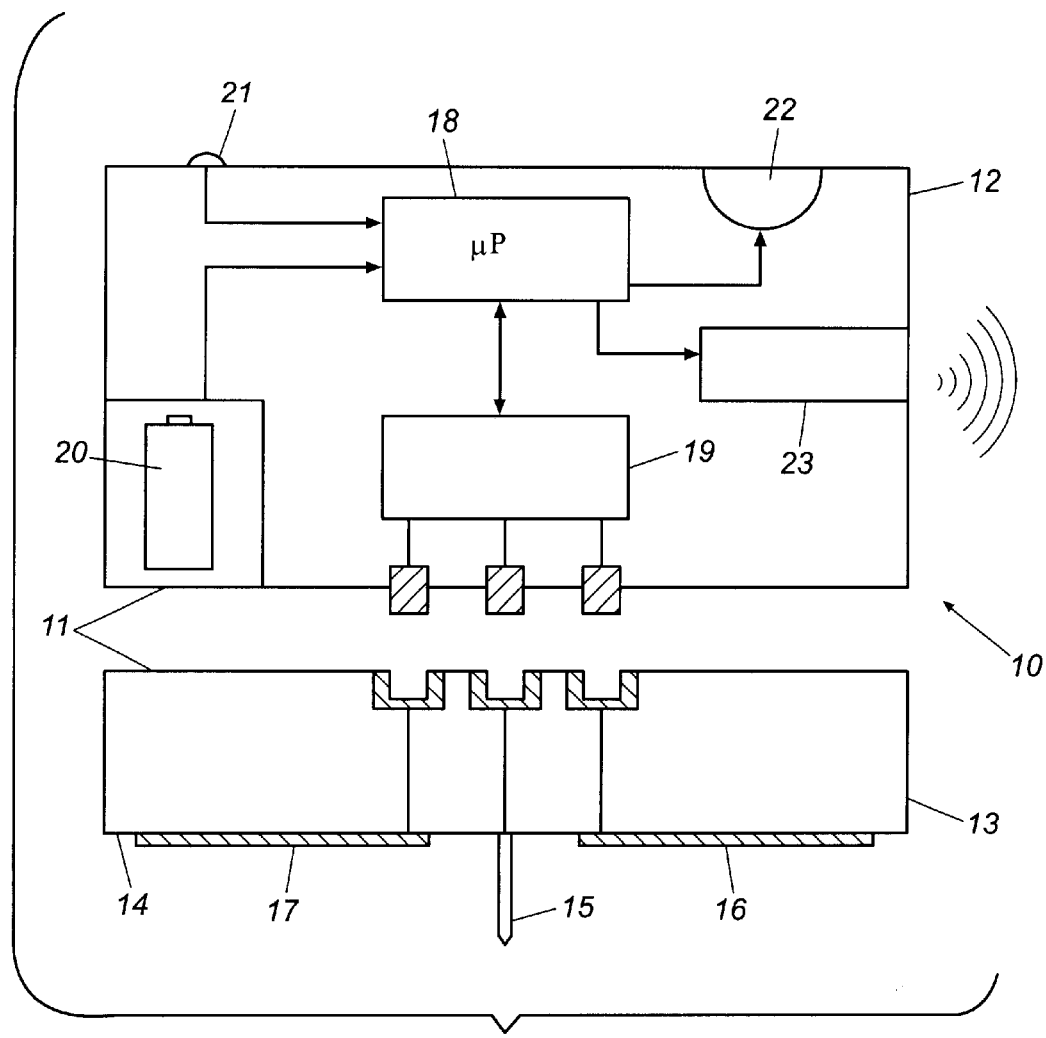
FIG. 1A is a schematic diagram of an analyte monitor device according to the invention.
Figure 1B:
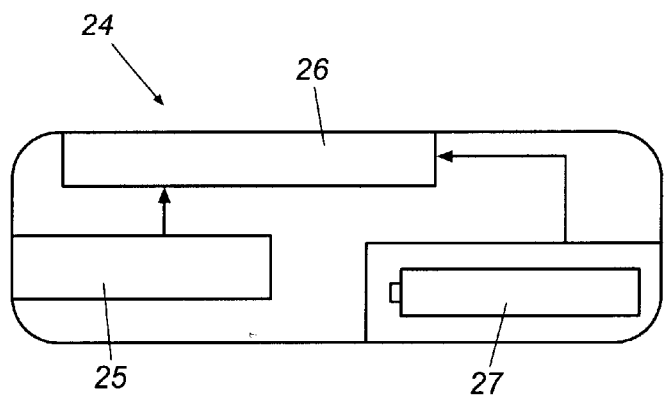
FIG. 1B is a schematic diagram of a display unit adapted for use with the monitor device of FIG. 1A.

FIG. 1A is a schematic illustration of an analyte monitor device for the in vivo measurement of an analyte according to the invention. FIG. 1B is a schematic illustration of a display unit, associated with the monitor device of FIG. 1A, for providing a visual output of the measured analyte levels.

The monitor device of FIG. 1A, indicated generally at 10, comprises a housing 11 separable into a first part 12 and a second part 13. The second part 13 of housing 11 has a lower surface 14 which is provided with a working electrode 15, a counter electrode 16 and a reference electrode 17. The device 10 is adhered to the skin of a subject by means of a conductive adhesive gel on the surfaces of counter electrode 16 and reference electrode 17.

Working electrode 15 is a platinum-iridium enzymatic sensor in the form of a needle the detailed structure of which will be described in detail below. Counter electrode 16 and reference electrode 17 are each in the form of a silver/silver chloride surface makes good electrical contact with the subject's skin by means of the adhesive gel thereon.

The electrodes 15,16,17 are connected to a microprocessor 18 via a voltage controller 19. Voltage controller 19 is adapted to supply constant voltages, pulsed voltages or varying voltages between the working electrode 15 and reference electrode 16. The voltage is controlled by the microprocessor 18, and both microprocessor 18 and voltage controller 19 are powered by a battery 20. A switch in the form of a push button 21 is used to stop or start the operation of the device, and an alarm 22 is provided to alert the user in the event of glucose levels being excessively high or low. The alarm 22 may also be used for a variety of other functions, such as to alert the user in the event of device malfunction or low battery levels, for example.

The monitor device 10 of FIG. 1A communicates with the display unit of FIG. 1B by means of a low power radio transmitter 23. The display unit of FIG. 1B, indicated generally at 24, is provided with a corresponding radio receiver 25, a visual LCD display 26, and a battery 27 to power the unit 24. Measured analyte levels from measuring device 10 can thus be transmitted to display unit 24.

Figure 2:
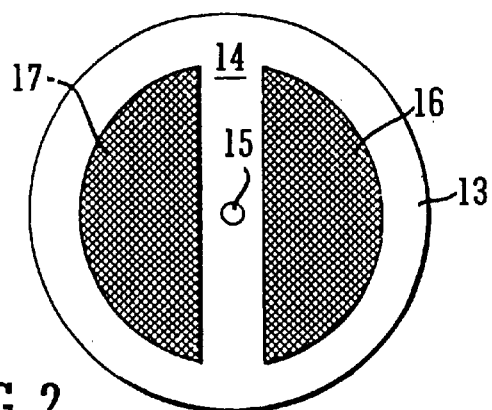
FIG. 2 is a view of the underside of the monitor device of FIG. 1A.

FIG. 2 shows a view of the underside of monitor 10. Thus, lower surface 14 of second part 13 is seen with working electrode 15 (i.e. the enzymatic sensor needle) in the centre. On either side, the counter electrode 16 and reference electrode 17, respectively, are represented by two approximately semi-circular cross hatched areas. The lower surface 14 is provided with a suitable adhesive to hold device 10 securely in place against the subject's skin.

Figure 3:
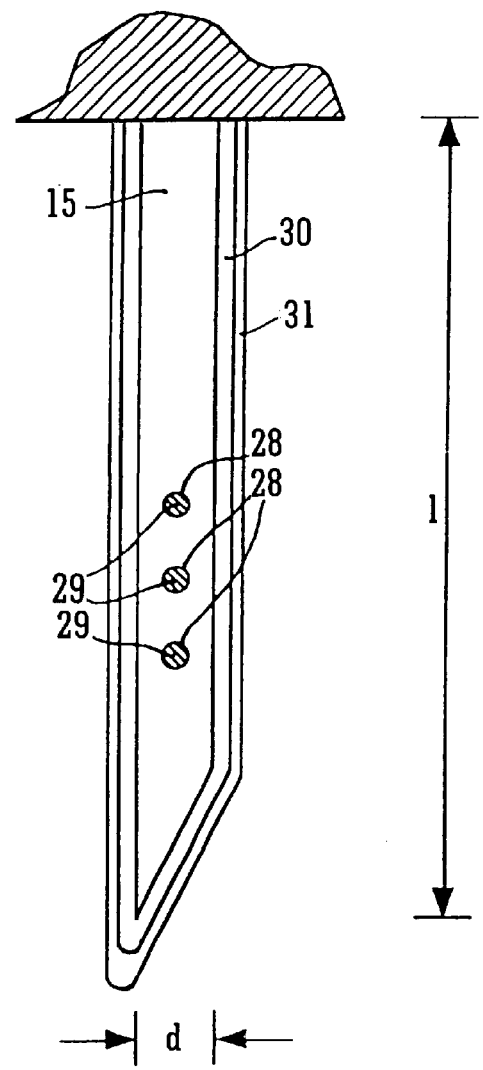
FIG. 3 is an enlarged elevation of the sensor needle of the monitor device of FIG. 1A.

The enzymatic sensor needle 15 is shown in FIG. 3 in elevation. The platinum-iridium needle 15 has a plurality of apertures 28 which contain the enzyme glucose oxidase 29. The glucose oxidase enzyme 29 is thus recessed from the surface of the needle 15 in order to protect the enzyme 29 from being physically damaged, for example, when the needle 15 punctures the skin of a patient.

A protective membrane 30 is provided on the surface of the needle 15, with an external coating of glucose 31 which is used for the purpose of calibrating the needle in vivo, as will be described below.

Membrane 30 is glucose-permeable and oxygen-permeable, but it is more permeable to oxygen than to glucose. This selective permeability helps to ensure that oxygen is in excess of glucose for the purpose of ensuring that the rate of reaction is not limited by an insufficient oxygen supply. This problem is discussed in more detail below. Suitable membrane materials include polyurethane, Nafion ("Nafion" is a Trade Mark for a perflourinated ion-exchange membrane), cellulose materials or polysiloxanes.

An alternative construction to that discussed above (protective membrane coated with glucose) is provided in which the protective membrane is applied with soluble glucose particles embedded therein. Upon application to a subject, the glucose dissolves to leave pores in the membrane. The size and distribution of the glucose particles is chosen beforehand to ensure that the pores provide the selective permeability to oxygen discussed above.

In FIG. 3, two dimensions are shown, namely the length l of the needle 15 and the diameter d of the needle 15. Suitable dimensions are a needle length 26 of 5 mm and a needle diameter 27 of 0.3 mm, although it will be appreciated that a wide variety of dimensions can be employed as required.

2. Operation

The basic principle of operation of the monitor device 10 is as follows. The monitor device 10 (comprising reusable first part 12, which includes the electronic controlling circuitry, and disposable second part 13, which includes the enzymatic sensor needle 15) is applied to a subject by removing a release liner (not shown) which protects adhesive lower surface 14 and sensor needle 15 before use, and then pressing lower surface 14 against the skin of a subject so that sensor needle 15 penetrates the skin of the subject and enters the subcutaneous region where it is in contact with subcutaneous tissue. The silver/silver chloride electrodes 16 and 17 lie in contact with the skin of the subject by means of their adhesive conductive coatings. The display unit 24 is worn on the wrist of the subject or is located in some other suitable location (such as by a bedside or in a nurse's station to allow monitoring by third parties of a patient's condition).

In use, glucose in the blood, plasma or serum present in the subcutaneous region diff-uses through protective membrane 30 as do oxygen and water. The glucose ($C_6H_{12}O_6$), oxygen ($O_2$) and water ($H_2O$) react in the presence of the glucose oxidase according to the reaction:

$$C_6H_{12}O_6 + O_2 + H_2O \rightarrow C_6H_{12}O_7 + H_2O_2,$$

thereby producing gluconic acid ($C_6H_{12}O_7$) and hydrogen peroxide ($H_2O_2$) at the sensor needle 15. Accordingly, the rate of hydrogen peroxide generation at platinum-iridium needle 15 is theoretically proportional to the concentration of glucose in the bloodstream.

The hydrogen peroxide produced at the surface of the platinum-iridium needle is oxidised (the platinum acts as a catalyst) according to the reaction:

$$H_2O_2 \rightarrow O_2 + 2H^+ + 2e^-.$$

Thus, the hydrogen peroxide serves as a source of electrons which are free to act as charge carriers if a potential is applied between the working electrode (sensor needle) 15 and the counter electrode 16.

The microprocessor 18 causes the voltage controller 19 to apply a voltage to the working electrode 15. The magnitude of the voltage is determined as a potential difference between the working electrode 15 and the reference electrode 17. However, no current flows between these two electrodes and instead the current flows through the counter electrode 16 (which is at the same potential as the reference electrode 17). In effect the circuit is a potentiostat, and the skilled person will be aware that this means that an accurate voltage can be applied to the working electrode relative to the counter-electrode, independent of the resistance between the electrodes, which might be expected to vary in individual cases.

Thus, when a voltage is applied to the working electrode 15, the microprocessor 18 measures the current flowing through the circuit of which the working electrode 15 and the counter electrode 16 form a part thereof. Since this current can only flow if free charge carriers are present, the current provides a measure of the number of charge carrying species in the vicinity of the working electrode 15. The majority of the current arises from the free electrons which are generated by the breakdown of hydrogen peroxide at the platinum (or platinum-iridium) needle surface.

As described in WO 96/14026, the voltage is only applied periodically between the working electrode 15 and the counter electrode 16. While the voltage between the working electrode and counter electrode is switched off, glucose reacts continuously with oxygen and water to generate increasing amounts of hydrogen peroxide at the sensor needle 15. By then applying a potential after it has been switched off for a given interval, all of the electrons generated by the hydrogen peroxide built up during the "off" interval are removed in a short burst of current which quickly decays to a steady state level, i.e. the level which would be detected if the voltage was applied continuously rather than intermittently.

By switching the voltage off and on repeatedly to allow a build up of hydrogen peroxide during the "off" interval and measuring accumulated hydrogen peroxide during the "on" interval, the measured contribution of charge carriers which arise from the breakdown of hydrogen peroxide is maximised relative to other charge carriers which might be present in the tissue of the user. Such other charge carriers give rise to a background level of current which is essentially constant over short periods of time.

The measured current is integrated by the microprocessor 18 to provide a measure of the total charge giving rise to the measured current: If Q represents the total charge of the combined charge carriers in a current flowing from 0 to t seconds, then:

$$\int_0^t I.dt = Q$$

Thus, by integrating the current over the duration of the applied voltage, an uncalibrated measure of the glucose concentration in the bloodstream is provided. The integration of a current pulse will be discussed further below having regard to FIG. 7.

While this type of enzymatic sensor needle has been described in relation to glucose, the principles may also be applied to other enzymatic sensors for detecting analytes other than glucose.

3. In vivo calibration

The batch of sensor needles of which sensor needle 15 forms a part thereof will have been calibrated in the factory. This is most usually achieved by taking a statistically representative sample of needles from a production batch, carrying out a laboratory calibration (using a standard glucose solution, for example) and applying the results of this calibration for all of the needles in the batch (presuming that the batch appears to be of acceptable quality. The calibration of this batch can be encoded on second part 13 of the monitor device 10. Preferably, this is achieved by using a machine readable encoding system (such as a bar code or a simple chip containing the calibration parameters) which is automatically read by the microprocessor when the first part 12 and the second part 13 are connected together, or when start button 21 is actuated.

As discussed above, however, the sensor needle may have undergone some changes during storage, and thus the calibration function determined during a laboratory test may not be entirely accurate when a needle is in use in vivo. More importantly, the interface between the needle and the surrounding body tissue will always give rise to at least slight variations between the performance of otherwise identical sensor needles because of differences between individuals and between individual application sites on the same individual.

Therefore, a further calibration occurs in vivo as follows. When the needle 15 enters the body, the glucose coating 31 dissolves almost immediately and saturates the glucose oxidase enzyme 29. The microprocessor provides a voltage to the electrodes and measures the resulting current. Because the enzyme is saturated by glucose, this first measured signal is a saturated or maximum measurable signal.

Figure 4A:
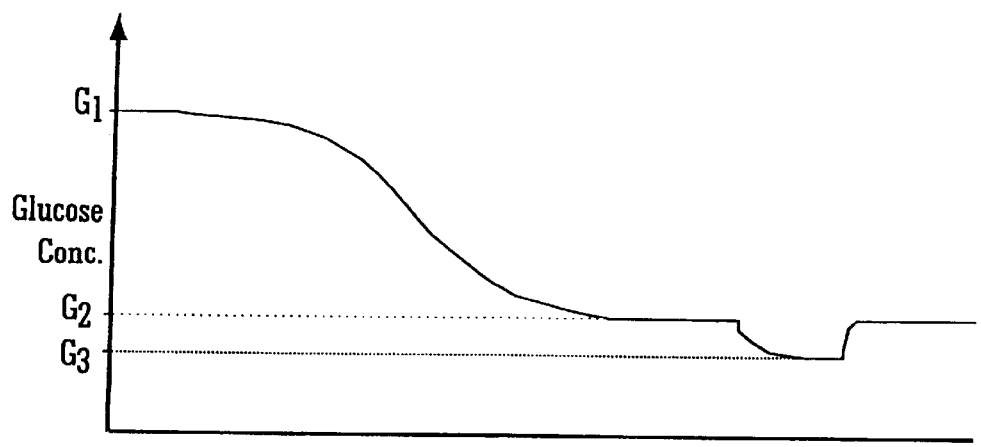
FIGS. 4A–4C are graphical representations of in vivo glucose levels in the vicinity of the sensor needle immediately after the monitor device of FIG. 1A is applied to a subject, the measured electrode current during the same period, and the applied electrode voltage during the same period, respectively.
Figure 4B:
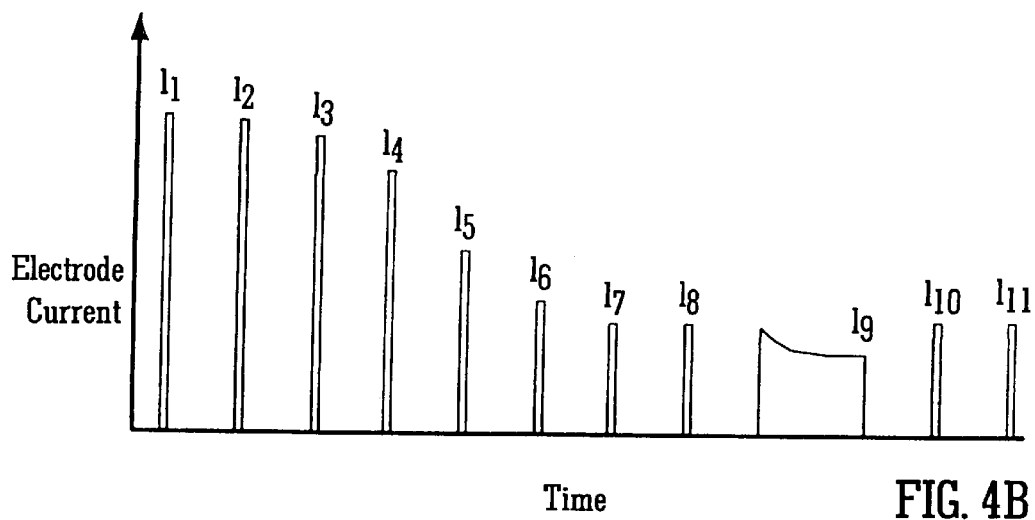
Figure 4C:
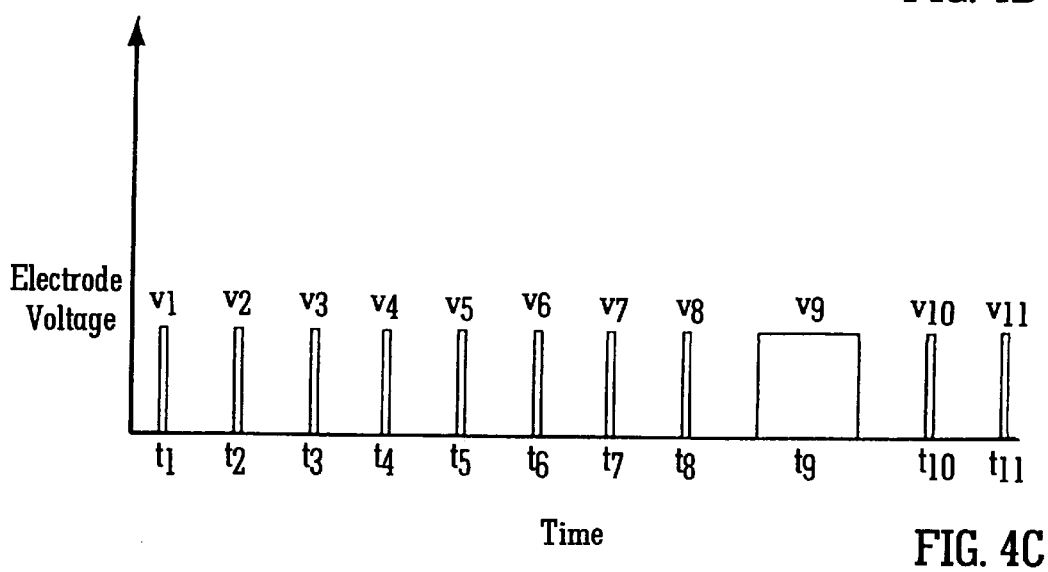

FIGS. 4A–4C are three graphs illustrating: (FIG. 4A) the in vivo glucose level for an interval of time immediately after the sensor needle 15 has been applied to the body; (FIG. 4B) the measured electrode current over the same interval; and (FIG. 4C) the periodic voltage pulses (which are generated by the voltage controller 19 under the control of microprocessor 18) applied to the electrodes and which give rise to the measured current shown in FIG. 4B.

A voltage $V_1$ (FIG. 4C) applied at time $t_1$ gives a current $I_1$ (FIG. 4B) which corresponds to the saturation level $G_1$ (FIG. 4A) of the enzyme. Although the glucose level will be initially above level $G_1$, the initial higher level is not shown as it is only the saturation level which can be measured by the sensor and which is of importance for the calibration method. Signal $I_1$ is stored in the memory of the microprocessor 18 as a first sensor signal.

Subsequent pulses $V_2$, $V_3$, $V_4$, etc. give rise to progressively lower signals $I_2$, $I_3$, $I_4$, etc. as the glucose diffuses away from the sensor needle 15 and is consumed in reaction with oxygen and water. The microprocessor 18 monitors the lowering signals until signals $I_7$ and $I_8$ are observed to be substantially equal. This indicates that glucose level G2 is the equilibrium glucose level, i.e. the concentration of glucose in the subcutaneous tissue of the patient at this time.

At this point, a prolonged pulse $V_9$ is applied which consumes all of the charge carriers at the sensor needle 15 due to hydrogen peroxide breakdown, i.e. giving a current signal $I_9$ which drops from a measure of the equilibrium glucose level $G_2$ to a measure of the background charge carrier level $G_3$ which is due to extraneous influences. Signal $I_9$ is also recorded by the microprocessor for calibration purposes.

After recording the first sensor calibration signal $I_1$ and the second sensor calibration signal $I_9$ the microprocessor resumes the intermittent pulsing $V_{10}$, $V_{11}$, etc.

Figure 7:
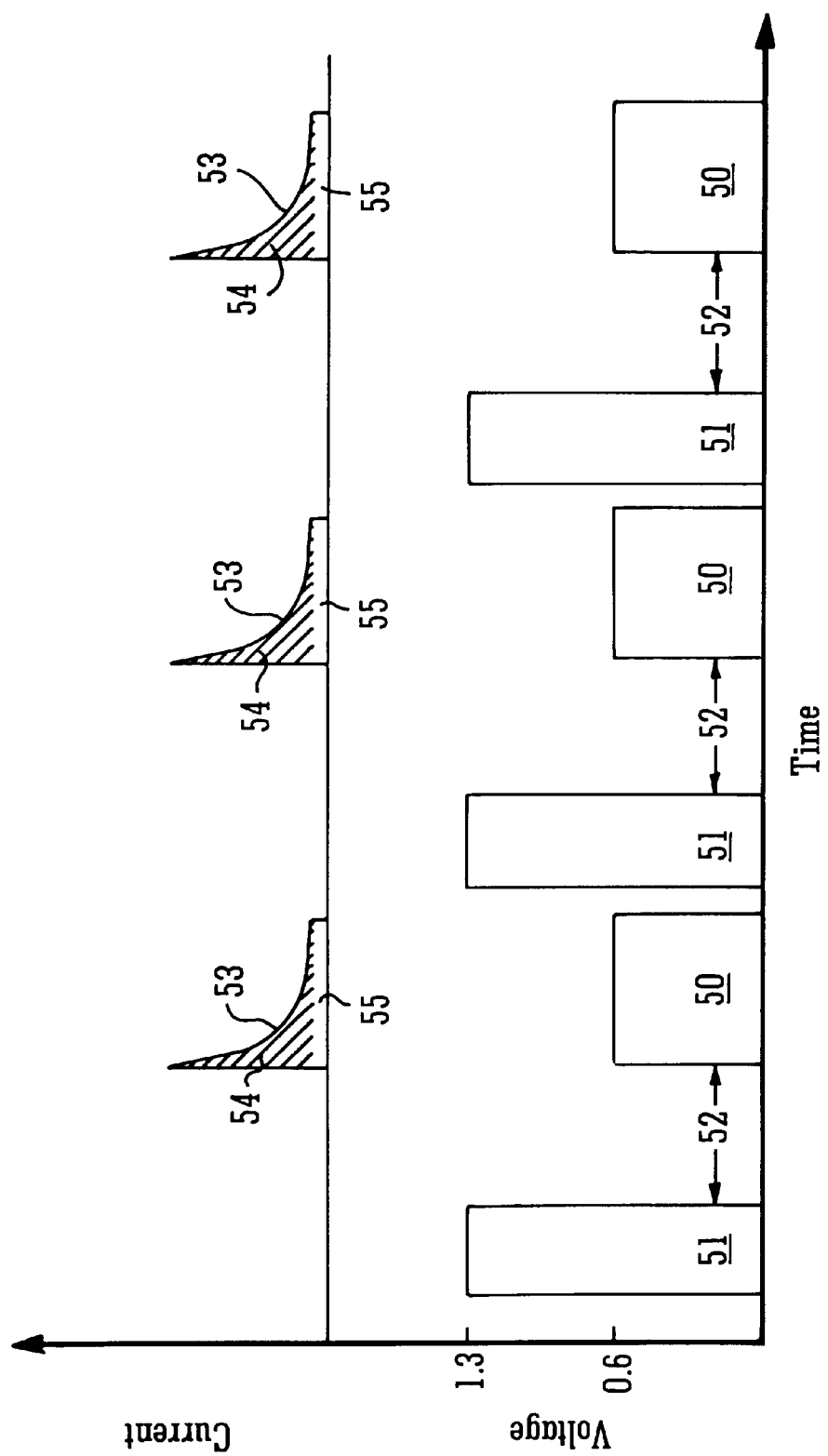
FIG. 7 is a graphical representation of applied electrode voltage and measured electrode current for an analyte monitor device according to the invention.

The scale and number of individual pulses in FIG. 7 relative to the overall timescale is not accurate, since a period of 5–10 minutes might typically be expected for the dissolution of glucose and its subsequent elimination by diffusion and enzymatic breakdown. During this time, a large number of pulses of short duration would be measured in practice.

When the first and second calibration signals $I_1$ and $I_9$ have been measured, the calibration function for this particular sensor needle 15 in this particular environment is calculated, and this can be explained with reference to FIG. 5.

Figure 5:
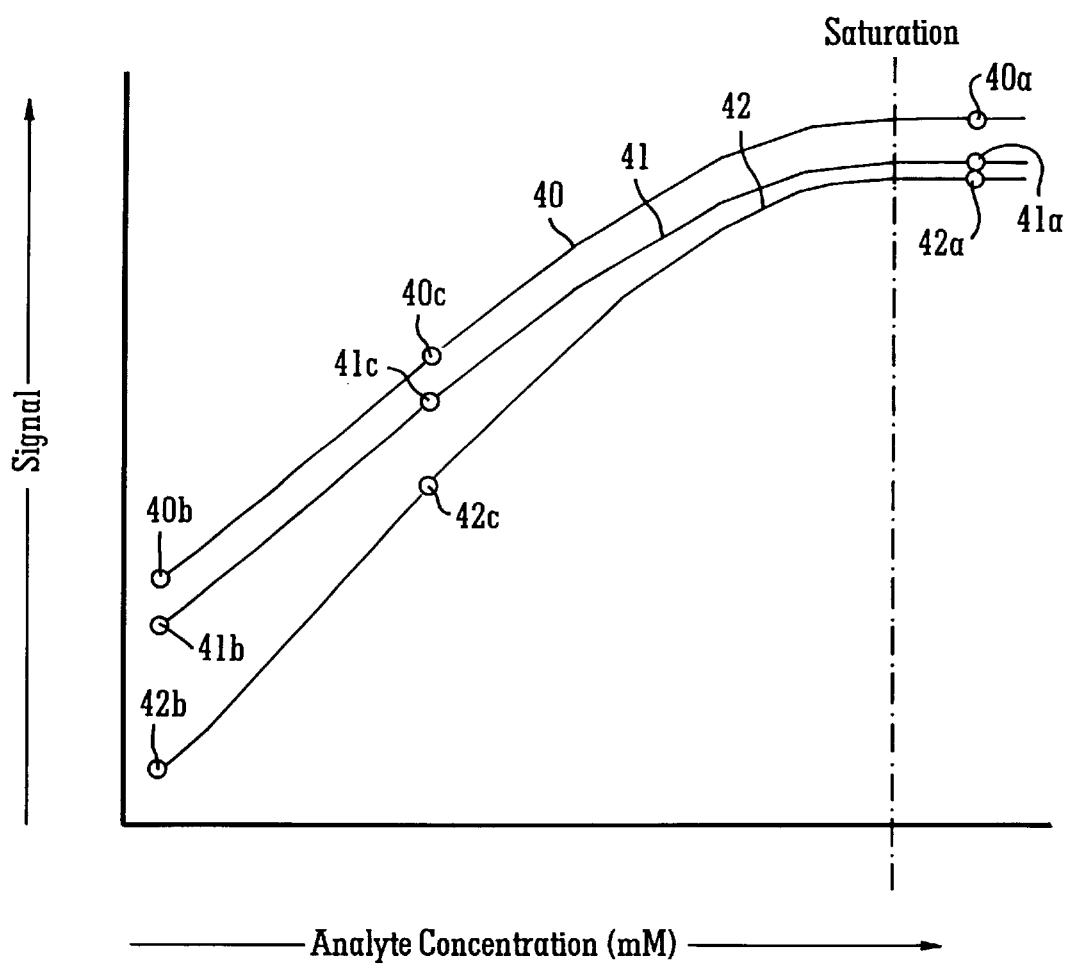
FIG. 5 is a plot of electrode current versus analyte concentration for an analyte monitor device according to the invention in three different environments.

FIG. 5 shows a plot of the characteristic performance curves of three different sensor needles from the same batch. The graph shows the signal measured in the case of each needle at different analyte concentrations:

Curve 40 is the theoretical or laboratory-calibrated performance curve measured in the manufacturing facility for the batch of sensor needles. This curve is the mean calibration curve for the batch of needles, measured from tests carried out on a statistically valid sample.

Curve 41 is the measured performance curve of a first sensor needle in vivo and curve 42 is the measured performance curve of a second sensor needle in vivo.

It will be seen that for each curve 40,41,42 there is a well-defined increase in signal strength for increasing analyte concentration. However, at a certain point the needle becomes saturated, and beyond this point, the signal strength does not increase with increasing analyte concentration.

The in vivo needle represented by curve 41 is calibrated as follows: shortly after it is applied to the subject, a maximum sensor signal 41$a$ is measured as described above ($I_1$). The amount of glucose provided on the sensor needle is sufficient to ensure that this signal will lie in the saturation region. As further described above, periodic pulses are then applied to the needle and this causes substantially all of the excess glucose in the vicinity of the needle to be consumed until the equilibrium glucose level $G_2$ is reached, following which a prolonged voltage pulse causes the glucose concentration to drop to a base line level ($G_3$). At this point the second sensor signal 41$b$ is measured as described above ($I_9$).

The microprocessor compares each of these signals 41$a$, 41$b$ with the corresponding signals on the theoretical or laboratory-measured signal-concentration curve 40 i.e. signal 41$a$ is compared with signal 40$a$ and signal 41$b$ is compared with signal 40$b$.

Since it is known that the calibration curves for needles from the same batch will all have the same basic shape, the calibration curve 41 for the in vivo sensor needle can be mapped onto the theoretical calibration curve 40 by mapping two known points on curve 41 to two known points on curve 40. In the case of both curves, the saturated signal value and the base line signal value has been measured, so a calibration function mapping any intermediate point from curve 41 onto curve 40 is easily derived.

Since the calibration parameters are encoded in the factory on the second part of the device, instructions are already provided for the microprocessor to calculate a calibrated output for any given point on the theoretical (laboratory measured) curve 40. The calculation of a calibration function mapping curve 41 onto curve 40 provides complete information for the microprocessor to provide a calibrated output for any subsequent measured signal which lies on curve 41.

In the case of curve 41, the calibration function involves increasing all signals by an amount corresponding to the constant vertical distance between curves 40 and 41. Thus, when a signal 41$c$ is measured, the microprocessor calculates the corresponding point 40$c$ and provides, as an output which is transmitted to the display unit, the calibrated measurement corresponding to point 40$c$ which can then be displayed in meaningful units.

The same basic principles apply to the calibration of the individual sensor needle which has characteristic measured curve 42. However, the calibration function must take into account the fact that the difference between the saturation signals 40$a$, 42$a$ is considerably less than the difference between the base line signals 40$b$, 42$b$. Thus, in order to map a measured point 42$c$ onto the corresponding point 40$c$ on theoretical curve 40, the microprocessor must apply a concentration-dependent calibration function in which the amount added to (or subtracted from) the measured signal 42$c$, when mapping this signal to point 40$c$, varies in accordance with the position of this point along curve 42$c$. Nevertheless, it will be appreciated that the similarity in basic shape between all three curves 40,41,42 makes the mapping of any measured curve to the theoretical curve a relatively simple operation, in which it is possible to deduce the mapping of the entire curve from a small number of measurements.

In certain cases it may be possible to use only one measurement. For example, if all sensors in a batch must provide a zero output whenever there is a zero level of analyte (no background signal), then a regular curve can be mapped onto the theoretical curve from only one measured point. Conversely, it may be desirable to employ three or more measurements in the calibration if sufficient accuracy cannot be obtained using two points.

The above-described calibration method enables expected variations in sensor behaviour to be compensated for. If the measurements are outside a given range (e.g. ±30% of the laboratory measured values) the microprocessor may be programmed to sound an alarm to indicate that the sensor is apparently defective and should not be used.

Figure 6:
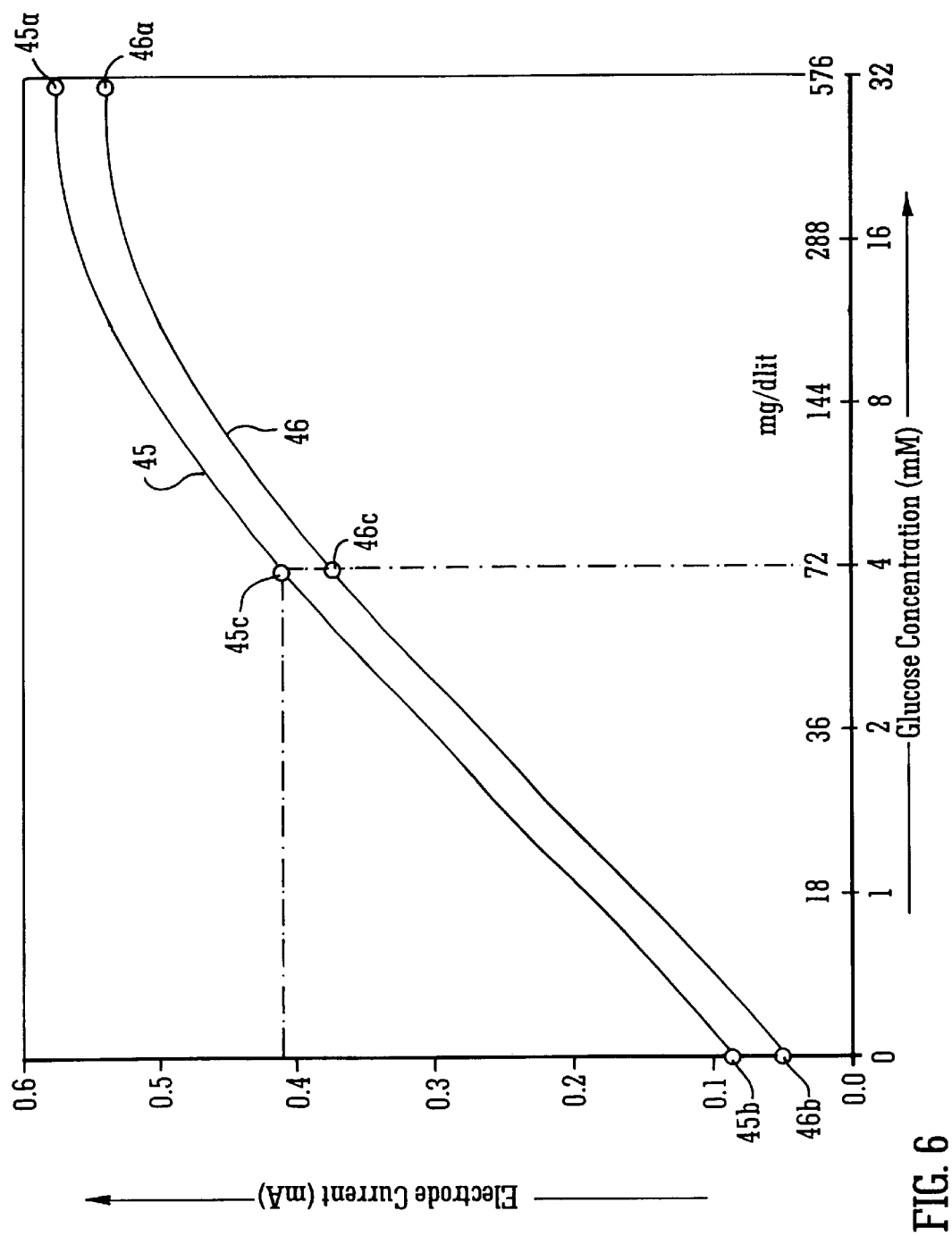
FIG. 6 is a plot of electrode current versus analyte concentration for an analyte monitor device according to the invention in two different environments.

FIG. 6 shows an example of the results of the calibration process achieved in an experimental trial. A calibrated reference curve 45 (obtained by calibration of the sensor needle in vitro) is shown, with end points 45a (saturation) and 45b (base line) as shown. A measured curve 46 is extrapolated by measuring saturation and base line end points 46a, 46b, respectively. From these measurements it is determined that the measured (in vivo) curve lies a constant 0.03 mA below the reference (laboratory calibrated) curve. Thus, a subsequent measurement 46c of 0.38 mA can then be correlated to a value of 0.41 mA on the reference curve, which in turn corresponds to a glucose concentration of 4 mM (72 mg/dlit).

It should be noted that the glucose concentration is shown on a logarithmic scale in which each equal step along the scale represents a doubling of glucose concentration. For this reason, it can be seen that the calibration function is extremely important, since a reading of 0.38 mA would otherwise be interpreted (from the reference curve) as relating to a glucose concentration of only slightly more than 3 mM.

4. In vivo Oxygen Generation

As can be seen from the chemical equation for the glucose/oxygen/water reaction set out above, the correct operation of the sensor presupposes that all of the glucose present in the vicinity of the glucose oxidase will react (at least up to the point where the sensor needle is saturated). The rate of reaction is, in theory, limited by the amount of glucose (and thus this reaction can be used to measure glucose). However, if in practice there is a lack of oxygen, then oxygen may become the limiting factor in the reaction, rather than glucose. The result of this is that the current level will provide an indication of the amount of oxygen rather than the amount of glucose.

A solution to this problem is illustrated in FIG. 7, in which the voltage is provided in two repeating series of pulses, namely a series of current measurement pulses 50 and a series of oxygen-generating pulses 51.

The series of current measurement pulses 50 of 0.6 V is used to measure current resulting from the hydrogen peroxide breakdown. The microprocessor measures the resulting electrode current 53 when these 0.6 V pulses are applied, and integrates the measured current 53 over the duration of the pulse to obtain a measurement of the charge carriers involved in the current pulse. As previously explained, the number of charge carriers is primarily determined by the amount of hydrogen peroxide generated by the reaction of glucose with oxygen and water. Each current pulse 53 is shown with a shaded area 54 which represents the additional current obtained by allowing the hydrogen peroxide to build up using a pulsatile measurement mode. The blank area 55 below shaded area 54 corresponds to the steady state current which would be obtained if there was no pulsatile measurement but instead there was a steady state measuring voltage.

In addition to the current measurement pulses 50, the series of oxygen-generating pulses 51 of 1.3 V is provided such that each 1.3 V pulse 51 immediately follows after a current measurement pulse 50. These oxygen-generating pulses 51 of 1.3 V serve to generate oxygen by electrolytically breaking down water. This generates a sufficient amount of oxygen to ensure that oxygen is in excess of glucose in the vicinity of the sensor needle, and it therefore follows that glucose is the limiting factor in the measurement process, ensuring an accurate measurement of glucose.

During the period when the oxygen generating pulse 51 is being applied across the electrodes, there will be a measurable electrode current which is not shown on the graph for purposes of clarity.

Following the generation of oxygen by an oxygen-generating pulse 51, the voltage is switched off for a period 52 of time to allow the glucose to react with the oxygen in the presence of glucose oxidase and produce hydrogen peroxide. The hydrogen peroxide breaks down at the needle 15 and when the current is switched on there is a current surge (as shown in the top half of the graph) which falls away to a base line level.

The time periods indicated in FIG. 7 are not shown to scale. Representative times for the current measurement pulses 50 are preferably 0.01s–1.0s, most preferably approximately 0.1s; for the oxygen-generating pulses 51 the time is also preferably 0.0s–1.0s, most preferably approximately 0.1s; and for the accumulation period 52 between the end of an oxygen-generating pulse 51 and the next current measurement pulse 50, the gap is preferably 0.05s–10s, most preferably approximately 1.0s. These times are given for reference purposes only, and depending on the particular circumstances, times lying outside these ranges may be suitable.

Figure 8:
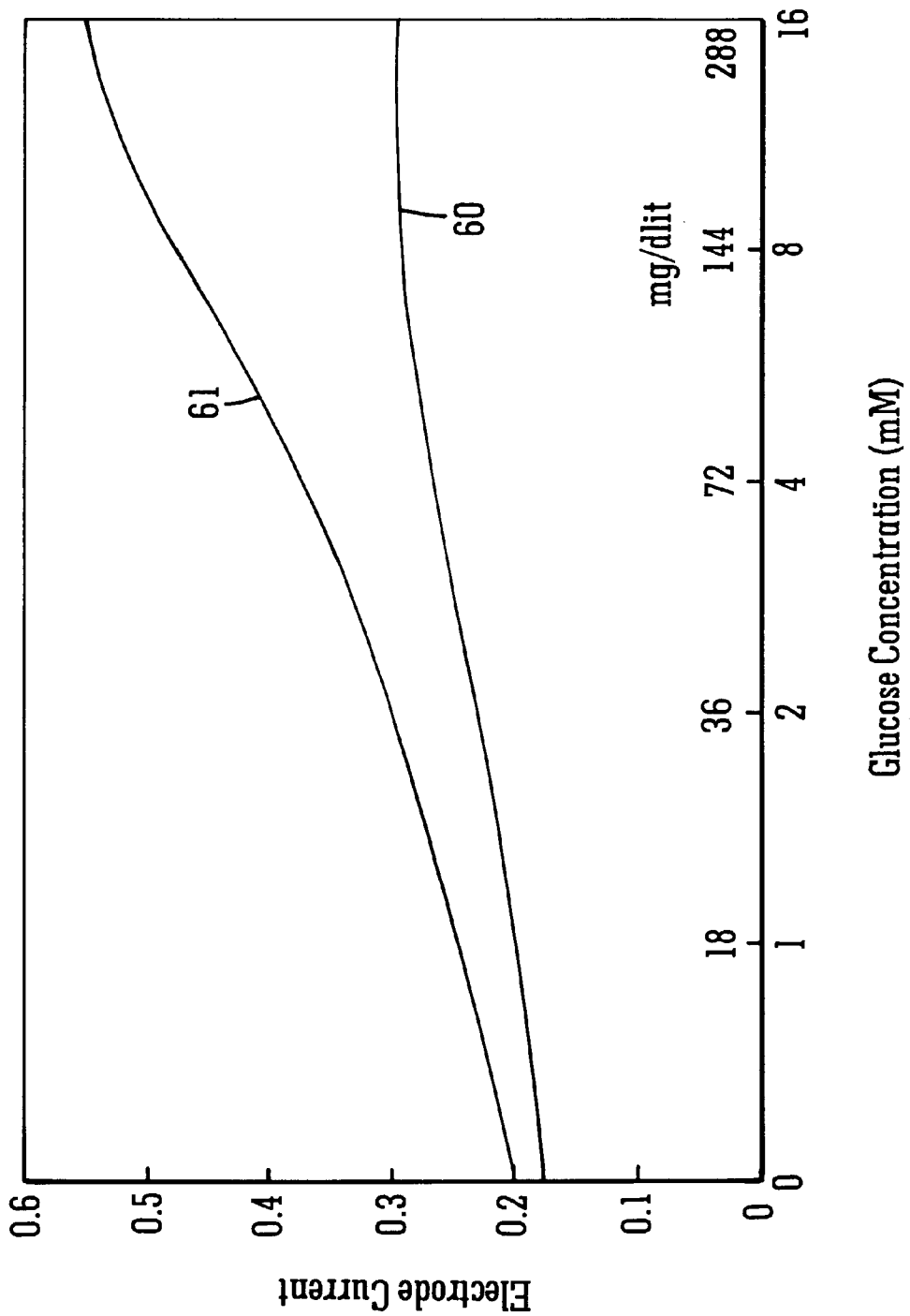
FIG. 8 is a comparative plot of electrode current against glucose concentration illustrating the effect of generating oxygen in vivo using a method according to the invention.

FIG. 8 shows the results of using a series of oxygen-generating pulse as described above. Curve 60 shows the average electrode current generated by a sensor such as sensor needle 15 at increasing glucose concentrations up to 16 mM. Curve 61 shows the current generated when an oxygen-generating pulse is included in the cycle. It can be seen that this causes a dramatic increase in the maximum level of current obtainable, as well as in the current range corresponding to the range of glucose concentrations illustrated. The advantage of having a larger current range is that a more accurate measurement of the glucose concentration becomes possible.

5. In vivo Testing of Sensor

Figure 9:
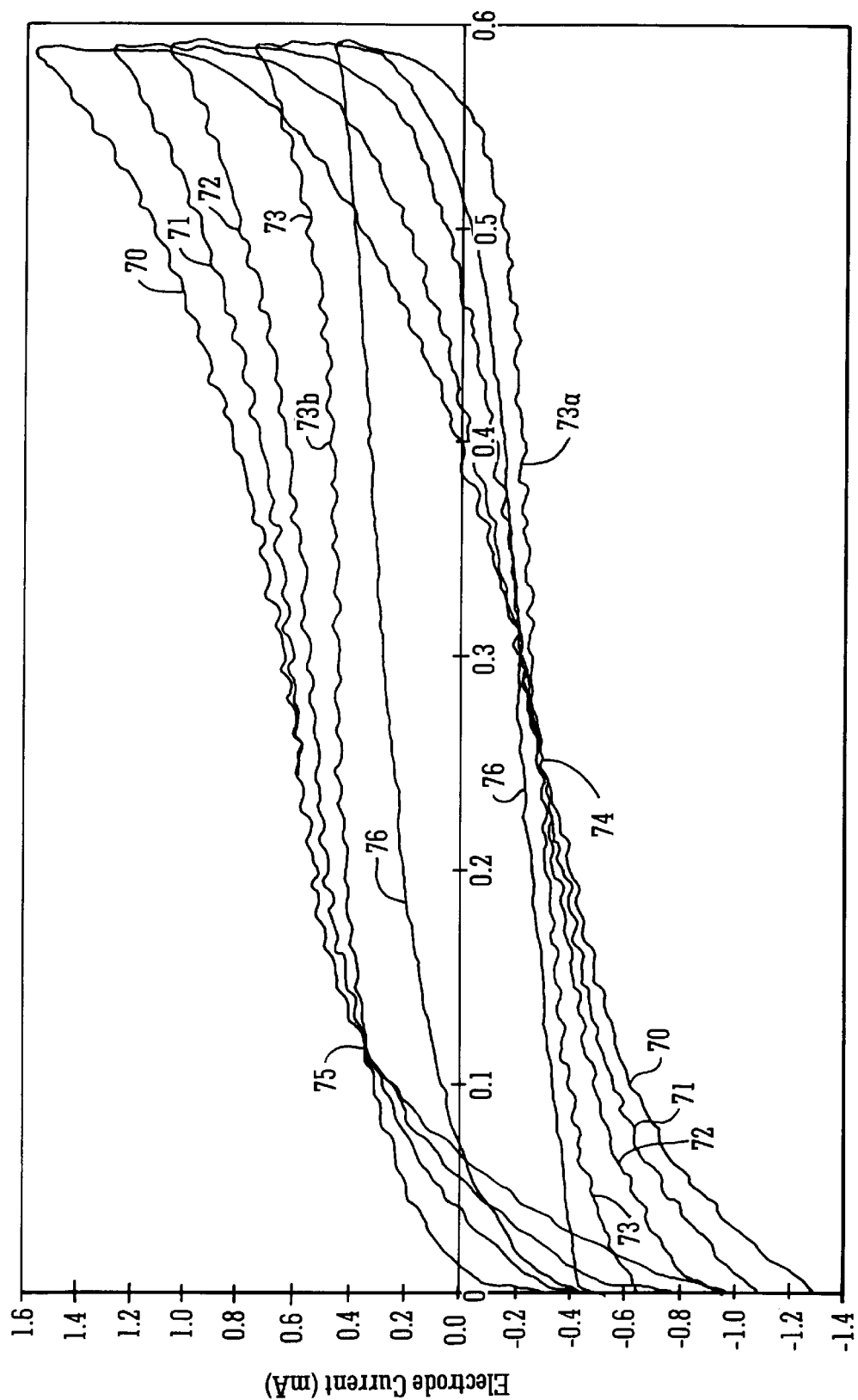
FIGS. 9 and 10 each show a series of current-voltage hysteresis cycles measured at a number of different glucose concentrations using a method according to the invention, together with a current-voltage hysteresis cycle for the same sensor after sensor deterioration.

As previously stated, the invention encompasses a method for the in vivo testing of an analyte sensor which is provided to a subject as an electrode of an electrical circuit. FIG. 9 illustrates how this method operates.

In FIG. 9, five current-voltage (I-V) characteristic curves are plotted. The curves show the current response to a cyclically varying voltage. The voltage is varied in each case through a cycle from 0.0 V to 0.58 V.

These cycles were measured in vitro using a sensor needle 15 as shown in FIG. 3. To simulate the in vivo situation in which the glucose level will fall from a saturation level to a background level, the current-voltage measurements were repeated at progressively lower concentrations, i.e. from an initial saturation level to a background level to obtain the I-V characteristics shown in FIG. 9. Curves 70, 71, 72 and 73 respectively are measured at levels of $9 \times 10^{-5}$ (units?), $6 \times 10^{-5}$ (units?), $3 \times 10^{-5}$ (units?), and zero (background level), respectively. Each voltage cycle took 20 s and in practice one might measure a hysteresis cycle 1–2 minutes for 5–15 minutes after application of the device to obtain hysteresis cycles corresponding to a range of glucose concentrations.

As can be seen, each of the I-V characteristic curves 70–73 exhibits hysteresis, i.e. the current values for the increasing voltage part of the each I-V curve are different to the current values for the decreasing voltage part of each curve. For example, the current measured at 0.4 V for the background level curve 73 has two different values. When the voltage is being increased from 0 V to 0.58 V, the current measured at 0.4 V is approximately −0.25 mA (denoted at 73a). After the voltage has reached 0.58 V and is decreased down to 0 V, it again passes through the level of 0.4 V, but a different current is measured, namely +0.5 mA (denoted at 73b).

As one would expect, different I-V characteristics are measured at different glucose concentrations. At two distinct nodal points, however, the four measured I-V curves 70–73 intersect: at a voltage of 0.26 V on the increasing part of each of the curves 70–73 (nodal point denoted at 74), the measured current level is −0.4 mA for all concentrations of glucose; and at a voltage of 0.12 V on the decreasing part of each of the curves 70–73 (nodal point denoted at 75), the measured current level is +0.35 mA for all concentrations of glucose.

Curve 76 is the I-V characteristic for the same needle after it has deteriorated somewhat. The most normal reason for needle deterioration in vivo is that the surface of the needle becomes coated with protein such as fibrin by the body. Any coating on the surface of the needle may adversely affect the reliability of the sensor needle, and so deterioration of the sensor needle used in the measurement of curves 70–73 has been simulated by the addition of a light coating of cellulose acetate. The needle is then reinserted into the subject and the cyclical I-V measurement is repeated to give curve 76.

The effect of this coating is that the shape of curve 76 is distorted such that it does not pass through the nodal points 74,75. While curve 76 passes close to nodal point 74, it is clearly far removed from nodal point 75, i.e. at a (decreasing) voltage of 0.12 V, the current level is approximately 1 mA whereas one would expect that the current level, irrespective of the glucose concentration, would be 0.35 mA.

In use, the microprocessor calculates a series of I-V curves 70–73 as the glucose level falls from the saturation level to the background level, and by comparing these curves, obtains and stores a value for one or more nodal points 74,75 at which the glucose level has no effect on the current-voltage response for a correctly functioning sensor.

Periodically thereafter (e.g. every 30 minutes or every hour), the microprocessor repeats the cyclical electrode voltage variation, and measures the current response. The current values at the voltages where nodal points were previously measured are then compared to the expected values, and any significant deviation indicates a deterioration in the functioning of the microprocessor.

Depending on the degree of accuracy required, the microprocessor may be programmed to sound an alarm if the measured current differs from the expected nodal point value by e.g. 10% or more. Thus, the user will be alerted in good time if the sensor needle requires replacement.

Figure 10:
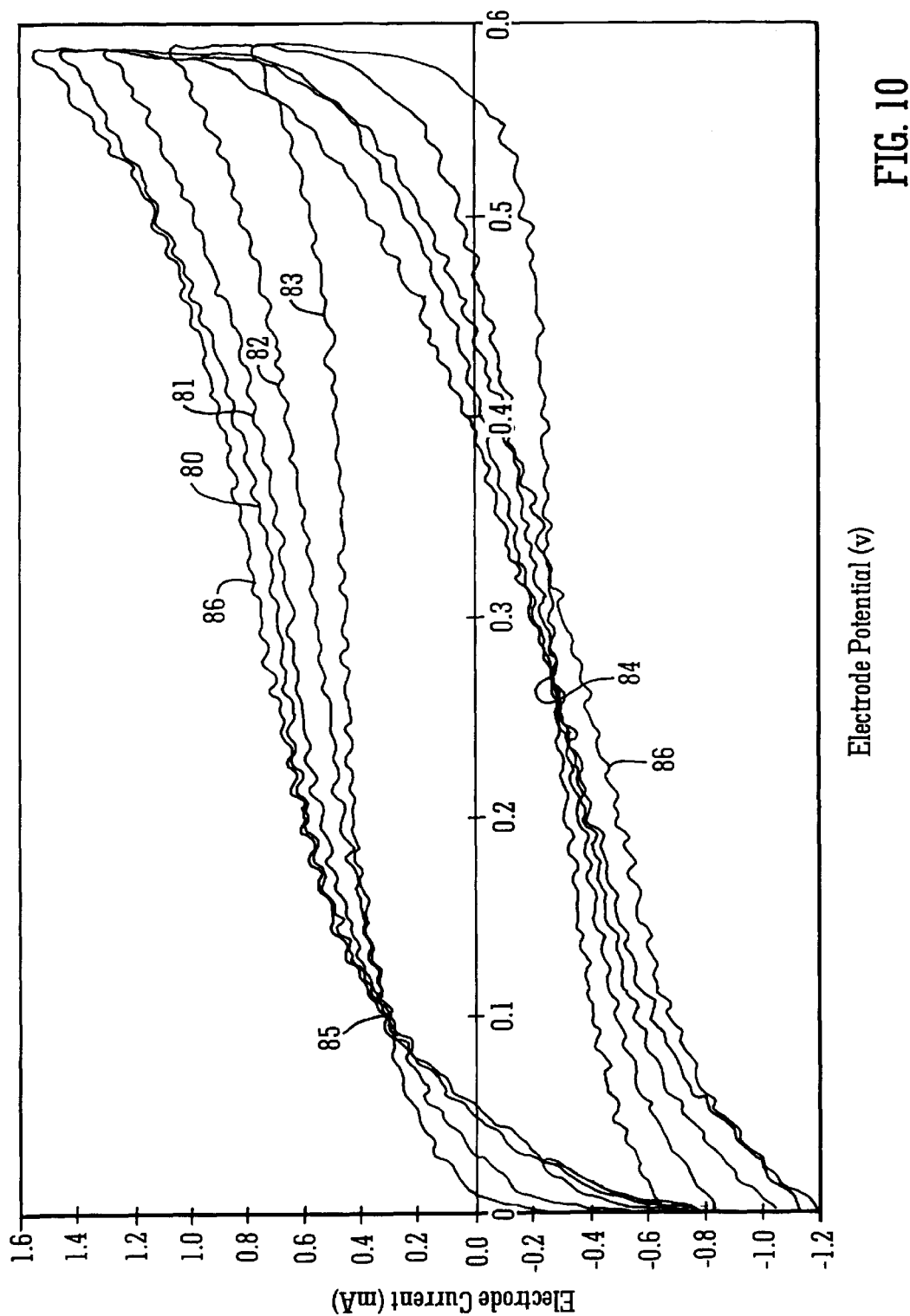

FIG. 10 shows a repetition of the measurements illustrated in FIG. 9, with curves 80, 81, 82 and 83 being I-V curves measured as the glucose concentration drops from a saturation level to a base line level. Nodal points 84 and 85 are easily identifiable. However, in this case instead of applying a coating of cellulose acetate, a coating of polyvinyl pyrrolidone (PVP) was used, and the resulting I-V curve 86 is plotted.

The effect of a PVP coating is more subtle than that of a cellulose acetate coating, in that curve 86 passes directly through nodal point 85. Nevertheless, curve 86 clearly does not pass through nodal point 84, and a difference of at least 0.1 mA can be measured, indicating the presence of the coating.

Figure 11:
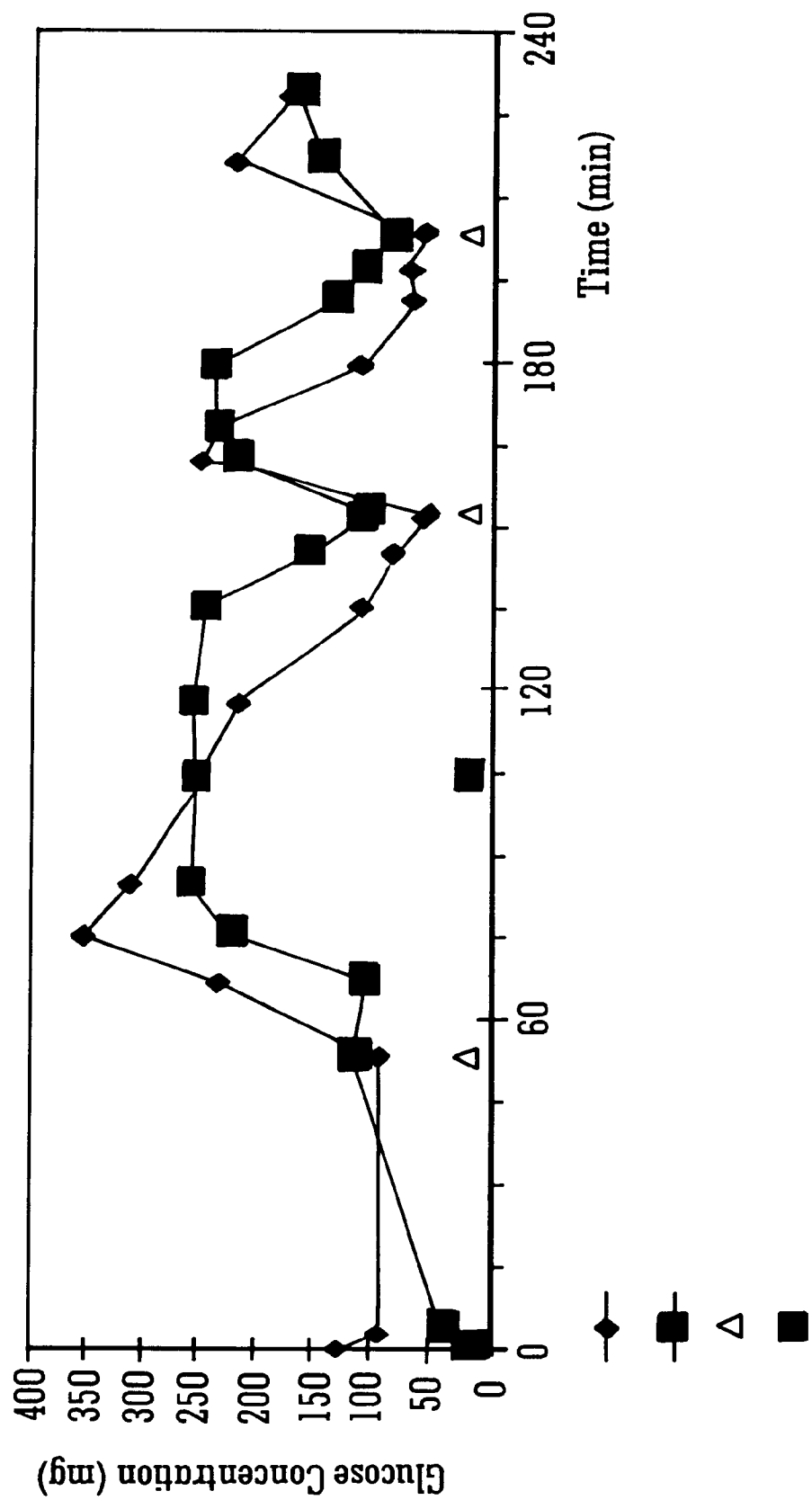
FIG. 11 is a plot of in vivo glucose concentration against time measured in tests carried out on a dog, comparing the results obtained using a device according to the invention as compared with standard reference tests.

FIG. 11 shows measurement results achieved with a glucose monitor according to the invention when compared to a reference average. Along the bottom of the graph are a series of black squares which indicate points at which insulin was delivered in an in vivo test on dogs. Open triangles indicate points at which glucose was delivered. The line joining the small diamonds shows the glucose concentration in mg/dlit and the line joining the large squares indicates the corresponding measurements made using electrodes according to the invention.

The reference line (small diamonds) is obtained from an average of four conventional glucose measurement tests, namely two analyses conducted by independent veterinary or medical laboratories, and two commercially available glucose testing kits ("Medisense" and "Elite"). The line denoting glucose monitors according to the invention was obtained from an average of three electrodes of the type illustrated in FIG. 3. It can be seen from these results that glucose monitors according to the invention closely mimic conventional methods of monitoring glucose levels.

The slight differences between the lines for the sensors according to the invention and the reference measurements can be explained by the fact that the reference line was obtained from the average of four tests using fresh whole blood samples from the cardiovascular system whereas the sensor according to the present invention was monitoring the glucose levels in subcutaneous tissue. Accordingly, while one expects to see an almost immediate increase in glucose levels in the intravenous system after glucose is administered intravenously, one expects to see a delay when the glucose measurement is made subcutaneously. Furthermore, one expects the sharp peaks and troughs measurable in blood samples to be smoothed out or averaged slightly in subcutaneous tissue because of the delay involved in blood diffusing into such tissue.

Figure 12:
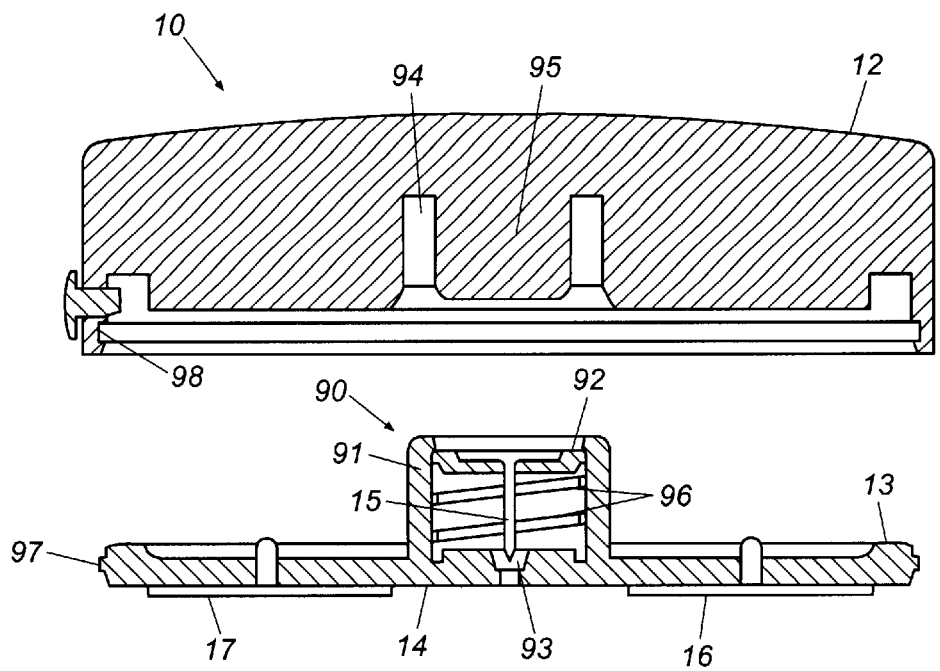
FIG. 12 is a sectional elevation of an embodiment of a device according to the invention before final assembly by the user.

FIG. 12 shows a schematic illustration of a needle deployment mechanism which can be used for an analyte monitor according to the invention. The embodiment of FIG. 12 is based on the embodiment discussed above in relation to FIGS. 1–3, and like parts are denoted by like reference numerals. Thus, the device 10 includes a first part 12 and a second part 13. Second part 13 has a lower surface 14 on which a reference electrode 16 and a counter electrode 17 are situated. A deployment mechanism, indicated generally at 90, carries sensor needle 15 which acts as a working electrode. Deployment mechanism 90 comprises a generally cylindrical casing 91 extending from second part 13. A platform 92 is movably mounted in casing 90, platform 92 carrying needle 15 on the underside thereof. Lower surface 14 of second part 13 is provided with an aperture 93 through which needle 15 can extend when platform 92 is caused to move downwards to the position shown in FIG. 13.

Figure 13:
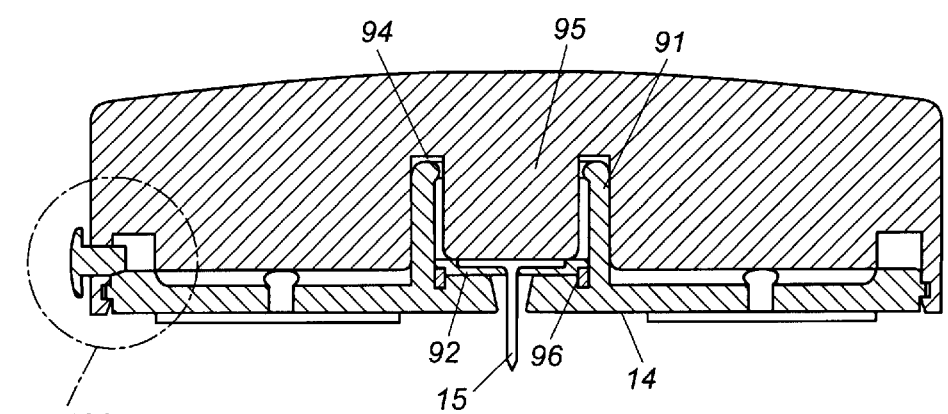
FIG. 13 is a sectional elevation of the device of FIG. 12 after final assembly.
Figure 13A:
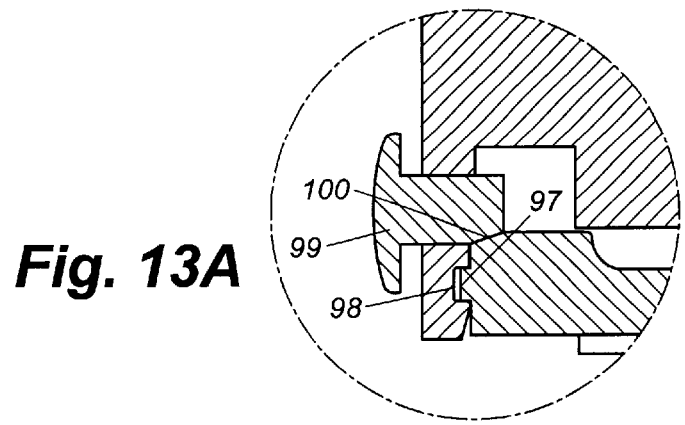
FIG. 13A is an enlarged detail of the device of FIG. 13.

As can be seen from FIG. 13, first part 12 of device 10 can be mated with second part 13 by means of an annular recess 94 in second part 13 which received cylindrical casing 91. Annular recess 94 defines a cylindrical projection 95 in the centre thereof. Cylindrical projection 95 causes platform 92 to be pushed downwards within cylindrical casing 91 when first part 12 is mated to second part 13. A spring 96 which biases platform 92 upwards resists the mating of first part 12 to second part 13, but a snap-fit mechanism defined by a lip 97 (see also FIG. 13A) on first part 12 and a groove 98 on second part 13, groove 98 corresponding to lip 97 such that lip 97 is retained within groove 98 when first part 12 is mated to second part 13 as shown in FIG. 13A.

The first part 12 and second part 13 are each provided with the requisite electrical connections (not shown) to connect the electrodes 15–17 to the electronic controlling circuitry provided in second part 13. Thus, the second part 13 can be a reusable electronic controller module and first part 12 can be a disposable electrode module. In order to replace the disposable electrode module which the first part 12 constitutes, a release button 99 is provided on the second part 13. FIG. 13A shows a detail of the device 10 in which a lip 97, groove 98 and release button 99 can be seen more clearly. The release button 99 is provided with a sloped surface 100 such that when the release button 99 is pushed towards the right, the sloped surface 100 exerts a downward force on the first part 12 to release the lip 97 from the groove 98. This allows the first part 12 to disengage from the second part 13, the disengagement being assisted by the spring 96 which tends to bias the platform 92 away from the lower surface 14.

The second part 13 can be provided with means for displaying the measured analyte level and/or with alarm means for indicating that the analyte level has passed beyond a pre-programmed limit. As an alternative to display means, the controller can be provided with a transmitter which transmits a suitable signal to a remote receiver which is provided with a display. This allows the monitor to warn the user discreetly, with the display being readable from a wristwatch-type display unit.

Figure 14:
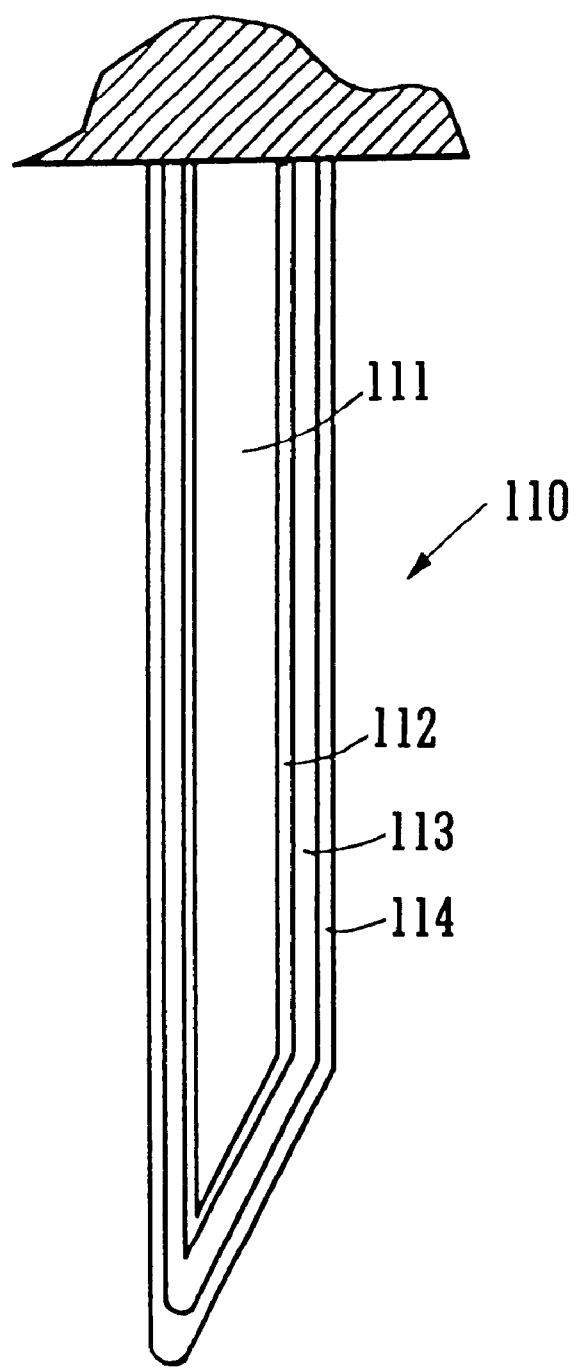
FIG. 14 is an elevation of an alternative construction of sensor needle to that shown in FIG. 3.

FIG. 14 shows an alternative construction of a sensor needle, indicated generally at 110, in which the platinum-iridium needle of FIG. 3 is replaced by a stainless steel needle shaft 111 on which a coating of platinum black 112 (otherwise referred to as colloidal platinum) is provided, with glucose oxidase enzyme embedded in the platinum black coating 112. This platinum black coating is coated by a protective polyurethane membrane 113 and this in turn is provided with a soluble glucose coating 114. The operation of the sensor needle 110 is essentially identical to that of the sensor needle 15 of FIG. 3, i.e. glucose reacts with oxygen and water in the presence of the enzyme embedded in the platinum black coating 112, thereby producing hydrogen peroxide which is catalysed by the colloidal platinum to provide free electrons.

It will be appreciated that the embodiments discussed above are preferred embodiments, falling within the scope of the appended claims, and that various alternative embodiments are contemplated.

What is claimed is:

1. A method of calibrating an analyte sensor in vivo, comprising the steps of:
   (a) providing a first predetermined stimulus to the sensor when the sensor is applied to a subject to produce a first sensor signal;
   (b) measuring the first sensor signal; and
   (c) determining a calibration function based on the first measured sensor signal resulting from the predetermined stimulus,
whereby the calibration function when applied to further signals received from the sensor can be used to provide a calibrated output.

2. A method according to claim 1, wherein the first predetermined stimulus is generated by providing a supply of material to which the sensor is sensitive, such that the material stimulates the sensor when the sensor is applied to a subject.

3. A method according to claim 2, wherein the material is provided in the vicinity of the sensor in a form in which it is soluble in biological fluids present in the area of the subject to which the sensor is applied.

4. A method according to claim 2, wherein the material comprises an analyte or a precursor or derivative thereof.

5. A method according to claim 1, wherein the predetermined stimulus is adapted to saturate the sensor such that the first signal is a maximum signal.

6. A method according to claim 1, further comprising the steps of providing a second predetermined stimulus to the sensor so as to produce a second sensor signal and measuring the second sensor signal, such that the determination of the calibration function is based on the first and second measured sensor signals.

7. A method according to claim 6, wherein the second sensor signal is a base line signal measured when substantially no analyte is in the vicinity of the sensor.

8. A method according to claim 7, wherein the second predetermined stimulus is provided by consuming substantially all of the analyte in the vicinity of the sensor.

9. A method according to claim 8, wherein the analyte is measured by the sensor by means of an electrochemical reaction, with the sensor forming part of an electrical circuit, and wherein the analyte is consumed by providing a current through the circuit which causes the analyte to undergo the electrochemical reaction, with the measurement of the second sensor signal being carried out shortly after the analyte is consumed.

10. A method according to claim 6, wherein the first and second signals constitute known points on a measured performance curve describing the measured performance of the sensor, and wherein the calibration function correlates the measured performance curve with a theoretical sensor performance curve for which there is stored a calibrated output, such that any further sensor signal measurement from the sensor can be calibrated by correlating the point on the measured performance curve to which the measurement relates with a corresponding point on the theoretical sensor performance curve, and hence with the corresponding calibrated output.

11. A method according to claim 10, wherein the known points on a curve describing the measured performance of the sensor are endpoints of the curve.

12. A method according to claim 1, wherein the analyte is glucose.

13. A method of measuring an analyte in vivo comprising the steps of applying a sensor to a subject, calibrating the sensor according to the method of claim 1, and providing a calibrated output of any further measurements made by the sensor based on the calibration function.

14. A device for the in vivo measurement of an analyte, comprising:
   (a) an in vivo sensor for measuring the analyte and providing a signal in response to the measurement of the analyte;
   (b) means for providing a first predetermined stimulus to the sensor when the sensor is applied to a subject so as to produce a first sensor signal; and
   (c) electronic circuitry associated with the sensor for receiving the signal and providing a calibrated output based on the signal, wherein the electronic circuitry includes means for determining a calibration function for the sensor based on the first measured sensor signal resulting from the predetermined stimulus;
such that the function when applied to further signals received from the sensor can be used to provide a calibrated output.

15. A device according to claim 14, wherein the means for providing a first predetermined stimulus to the sensor comprises a supply of material associated with the sensor such when the sensor is applied to a subject, the sensor is sensitive to the material.

16. A device according to claim 15, wherein the supply of material is associated with a permeable protective coating provided on the sensor.

17. A device according to claim 15, wherein the supply of material is provided in an amount sufficient to saturate the sensor and thereby generate a maximum signal which can be used to calibrate the sensor.

18. A device according to claim 15, wherein the sensor comprises an element which is adapted to be inserted subcutaneously, intradermally, intravenously or by surgical implantation into the subject, and wherein the supply of material is provided on the sensor in soluble form.

19. A device according to claim 15, further comprising a housing having a lower surface for application to the skin of a subject, wherein the sensor is in the form of a needle extending from the housing such that the sensor penetrates the skin of the subject when the device is applied thereto.

20. A device according to claim 15, wherein means are provided for generating a base line signal corresponding to the signal obtained when substantially no analyte is present in the vicinity of the needle, and wherein the base line signal is used to calibrate the sensor.

21. A device according to claim 20, wherein the means for generating a base line signal comprises a voltage generator which forms part of the electronic circuitry, and wherein the base line signal is provided by passing a current in the vicinity of the needle which eliminates the analyte or a chemical substance used in the measurement of the analyte.

22. A device according to claim 15, wherein the analyte is glucose.

23. A method for the in vivo testing of an analyte sensor which is provided to a subject as an electrode of an electrical circuit, comprising the steps of:
 (a) applying a potential to the electrode and varying the electrode potential so as to cause the electrode current to undergo at least part of a cycle which exhibits hysteresis;
 (b) measuring and recording a plurality of current values on the hysteresis cycle;
 (c) calculating a characteristic point on the hysteresis curve from the plurality of current values; and
 (e) comparing the characteristic point with a stored value and determining from this comparison whether the sensor meets a predetermined condition.

24. A method according to claim 23, wherein the characteristic point is a nodal point on the hysteresis curve.

25. A method according to claim 23, wherein the nodal point is defined as a voltage for which the current value is independent of the analyte concentration in the vicinity of the sensor when the sensor is operating correctly.

26. A method according to claim 23, wherein steps (a)–(e) are repeated periodically.

27. A method according to claim 23, wherein an initial iteration of steps (a)–(d) yields a value for the characteristic point which is stored for comparative subsequent use.

28. A method according to claim 27, wherein the initial iteration is repeated a plurality of times shortly after the sensor has been applied to the subject, and wherein a supply of the analyte to be measured is provided to the sensor in varying concentrations during the repetition of the iterations.

29. A method according to claim 28, wherein the analyte is supplied on the sensor in such a manner that it is released upon application of the sensor to the subject, and wherein the varying concentrations of analyte are achieved by consuming the analyte in a reaction or allowing the analyte to diffuse within the body of the subject.

30. A method according to claim 23, further comprising the step of providing an indicator if it is determined that the sensor does not meet the predetermined condition.

31. A method according to claim 30, wherein the indicator comprises an audible alarm.

32. A device for the in vivo measurement of an analyte, comprising:
 (a) an in vivo sensor for measuring the analyte and providing a signal in response to the measurement of the analyte;
 (b) electronic circuitry associated with the sensor for receiving the signal and providing a calibrated output based on the signal;
 (c) an electrical circuit in which the sensor acts as an electrode, the electrical circuit comprising means for energizing the electrode to a predetermined potential and for measuring and recording the resultant current through the electrode;
 (d) means for varying the electrode potential so as to cause the current to undergo at least part of a hysteresis cycle;
 (e) means for calculating a characteristic point on the hysteresis curve from the recorded current measurements; and
 (f) means for comparing the characteristic point with a stored value and for determining from this comparison whether the sensor meets a predetermined condition.

33. A device according to claim 32, wherein the characteristic point is a nodal point on the hysteresis curve.

34. A device according to claim 32, wherein the nodal point is defined as a voltage for which the current value on the hysteresis curve is independent of the analyte concentration in the vicinity of the sensor when the sensor is functioning correctly.

35. A device according to claim 32, further comprising a memory for storing the value of a characteristic point determined on an initial iteration of measurements of current values.

36. A device according to claim 32, further comprising means for providing an alarm if it is determined that the sensor does not meet the predetermined condition.

37. A method for the in vivo measurement of an analyte, comprising:
 (a) providing an in vivo sensor, which acts as an electrode of an electrical circuit, to a subject for measuring the analyte, wherein the operation of the sensor is dependent on a reaction in which oxygen is required;
 (b) passing a voltage through the electrode, the voltage being of a magnitude and duration sufficient to cause the electrolysis of a chemical species present in the vicinity of the sensor so as to generate oxygen;
 (c) measuring the signal produced by the sensor in response to the oxygen-dependent reaction; and
 (d) repeating steps (b) and (c) periodically.

38. A method according to claim 37, wherein water is the chemical species present in the vicinity of the sensor which is electrolyzed to provide oxygen.

39. A method according to claim 37, wherein step (b) continues for a duration sufficient to generate oxygen in an excess stoichiometric ratio relative to the analyte being measured at the sensor.

40. A device for the in vivo measurement of an analyte, comprising:
 (a) an in vivo sensor for measuring the analyte and providing a signal in response to the measurement of the analyte, wherein the operation of the sensor is dependent on a reaction in which oxygen is required;
 (b) electronic circuitry associated with the sensor for receiving the signal and providing a calibrated output based on the signal;
 (c) an electrical circuit in which the sensor acts as an electrode, the electrical circuit comprising means for energizing the electrode to a voltage which is of a magnitude and duration sufficient to cause the electrolysis of a chemical species present in the vicinity of the sensor to provide oxygen; and (d) means for alternately generating oxygen by electrolysis and measuring the analyte by allowing the generated oxygen to take part in the reaction.

41. A device according to claim 14, further comprising means for delivering a substance to the subject in response to the measured analyte values.

42. A device according to claim 32 further comprising means for delivering a substance to the subject in response to the measured analyte values.

43. A device according to claim 40 further comprising means for delivering a substance to the subject in response to the measured analyte values.

44. A device according to claim 41, wherein the substance is a medicament suitable to correct a condition in the patient for which the analyte is an indicating agent.

45. A device according to claim 42, wherein the substance is a medicament suitable to correct a condition in the patient for which the analyte is an indicating agent.

46. A device according to claim 43, wherein the substance is a medicament suitable to correct a condition in the patient for which the analyte is an indicating agent.

47. A device for calibrating an analyte sensor in vivo, comprising:
   (a) a sensor for application to a subject;
   (b) means for providing a first predetermined stimulus to the sensor to produce a first sensor signal;
   (c) means for measuring the first sensor signal; and
   (d) means for determining a calibration function based on the first measured sensor signal resulting from the predetermined stimulus,
whereby the calibration function when applied to further signals received from the sensor can be used to provide a calibrated output.

48. A device according to claim 47, wherein the means for providing the first predetermined stimulus comprises a supply of material to which the sensor is sensitive, such that the material stimulates the sensor when the sensor is applied to a subject.

49. A device according to claim 48, wherein the material is soluble in biological fluids present in the area of the subject to which the sensor is applied.

50. A device according to claim 47, wherein the material comprises an analyte or a precursor or derivative thereof.

51. A device according to claim 47, wherein the predetermined stimulus is adapted to saturate the sensor such that the first signal is a maximum signal.

52. A device according to claim 47, further comprising means for providing a second predetermined stimulus to the sensor so as to produce a second sensor signal and means for measuring the second sensor signal, such that the means for determination of the calibration function determines a calibration function based on the first and second measured sensor signals.

53. A device according to claim 52, wherein the second sensor signal is a base line signal measured when substantially no analyte is in the vicinity of the sensor.

54. A device according to claim 52, wherein the second predetermined stimulus is provided by consuming substantially all of the analyte in the vicinity of the sensor.

55. A device according to claim 47, wherein the first and second signals constitute known points on a measured performance curve describing the measured performance of the sensor, and wherein the calibration function correlates the measured performance curve with a theoretical sensor performance curve for which there is stored a calibrated output, such that any further sensor signal measurement from the sensor can be calibrated by correlating the point on the measured performance curve to which the measurement relates with a corresponding point on the theoretical sensor performance curve, and hence with the corresponding calibrated output.

56. A device according to claim 55, wherein the known points on a curve describing the measured performance of the sensor are endpoints of the curve.

57. A device according to claim 47, wherein the analyte is glucose.

58. A device for measuring an analyte in vivo comprising means for applying a sensor to a subject, means for calibrating the sensor according to the method of claim 1, and means for providing a calibrated output of any further measurements made by the sensor based on the calibration function.

59. A sensor for use in a device according to claim 47.

* * * * *

UNITED STATES PATENT AND TRADEMARK OFFICE
CERTIFICATE OF CORRECTION

| | | |
|---|---|---|
| PATENT NO. | : 6,275,717 B1 | Page 1 of 1 |
| APPLICATION NO. | : 09/102840 | |
| DATED | : August 14, 2001 | |
| INVENTOR(S) | : Joseph Gross et al. | |

It is certified that error appears in the above-identified patent and that said Letters Patent is hereby corrected as shown below:

On the Title Page, at Item 60, insert the following:

-- Related U.S. Application Data

Provisional Application No. 08/881,547** filed on June 24,1997.

**A petition to convert Non-provisional Application No. 08/881,547 to a provisional application was filed on June 9, 1998, and received by the U.S. Patent and Trademark Office on June 12, 1998, but the Office has not assigned a provisional patent application number to this application. --

At column 1, line 5, under the title, insert the following :

-- CROSS-REFERENCE TO RELATED APPLICATIONS

This application claims priority to U.S. Provisional Patent Application Serial No. [unassigned] filed June 24, 1997, as U.S. Non-provisional Patent Application Serial No. 08/881,547 and requested to be converted to a provisional application on June 9, 1998, by way of a petition received by the U.S. Patent and Trademark Office on June 12, 1998. Due to an oversight by the Office, Application No. 08/881,547 was not assigned a provisional application number. --

Signed and Sealed this
Eighth Day of November, 2011

David J. Kappos
*Director of the United States Patent and Trademark Office*